(12) United States Patent
Hunter et al.

(10) Patent No.: US 9,920,124 B2
(45) Date of Patent: Mar. 20, 2018

(54) METHODS OF PRODUCING IMMUNOCONJUGATES

(71) Applicant: MEDIMMUNE, LLC, Gaithersburg, MD (US)

(72) Inventors: Alan Hunter, Gaithersburg, MD (US); Thomas Linke, Gaithersburg, MD (US); Timothy Pabst, Gaithersburg, MD (US); Michaela Wendeler, Gaithersburg, MD (US); Xiangyang Wang, Gaithersburg, MD (US); Christopher Thompson, Gaithersburg, MD (US); Guoling Xi, Gaithersburg, MD (US); Andrew Fulton, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/654,384

(22) PCT Filed: Dec. 19, 2013

(86) PCT No.: PCT/US2013/076625
§ 371 (c)(1),
(2) Date: Jun. 19, 2015

(87) PCT Pub. No.: WO2014/100443
PCT Pub. Date: Jun. 26, 2014

(65) Prior Publication Data
US 2015/0337040 A1    Nov. 26, 2015

Related U.S. Application Data

(60) Provisional application No. 61/740,111, filed on Dec. 20, 2012.

(51) Int. Cl.
| | |
|---|---|
| *C07K 16/00* | (2006.01) |
| *C07K 17/00* | (2006.01) |
| *C07K 19/00* | (2006.01) |
| *C07K 1/36* | (2006.01) |
| *A61K 39/44* | (2006.01) |
| *C07K 16/28* | (2006.01) |
| *C07K 16/30* | (2006.01) |
| *C07K 14/21* | (2006.01) |
| *C07K 1/113* | (2006.01) |
| *A61K 39/395* | (2006.01) |

(52) U.S. Cl.
CPC .... *C07K 16/2851* (2013.01); *A61K 39/39591* (2013.01); *C07K 1/1136* (2013.01); *C07K 1/36* (2013.01); *C07K 14/21* (2013.01); *C07K 16/2803* (2013.01); *C07K 16/30* (2013.01); *C07K 2317/14* (2013.01); *C07K 2317/56* (2013.01); *C07K 2319/55* (2013.01)

(58) Field of Classification Search
None
See application file for complete search history.

(56) References Cited

U.S. PATENT DOCUMENTS

| | | | | |
|---|---|---|---|---|
| 2005/0037002 A1* | 2/2005 | Velardi | ................ | C07K 16/28 424/143.1 |
| 2008/0125580 A1* | 5/2008 | Pizarro | ................... | C07K 1/36 530/399 |
| 2009/0305411 A1* | 12/2009 | FitzGerald | ......... | C07K 16/2803 435/377 |

FOREIGN PATENT DOCUMENTS

| | | |
|---|---|---|
| EP | 1 845 103 A1 | 10/2007 |
| WO | WO 2012/015912 A1 | 2/2012 |

OTHER PUBLICATIONS

Arakawa et al. (Protein Expression and Purification, 2004, 36:244-248).*
Katoh, et al., "Continuous Refolding of Lysozyme with Fed-Batch Addition of Denatured Protein Solution", Process Biochemistry, 2000, vol. 35, No. 10, pp. 1119-1124.
Chen, et al., "Adsorptive Refolding of a Highly Disulfide-Bonded Inclusion Body Protein Using Anion-Exchange Chromatography", Journal of Chromatography A, 2009, vol. 1216, No. 24, pp. 4877-4886.
Shiraki, et al., "Biophysical Effect of Amino Acids on the Prevention of Protein Aggregation", J. Biochem., 2002, vol. 132, No. 4, pp. 591-595.
Tsumoto, et al., "Role of Arginine in Protein Refolding, Solubilization, and Purification", Biotechnol. Prog., 2004, vol. 20, No. 5, pp. 1301-1308.
Mannall, et al., "Factors Affecting Protein Refolding Yields in a Fed-Batch and Batch-Refolding System", Biotechnology and Bioengineering, 2007, vol. 97, No. 6, pp. 1523-1534.
Linke, et al., "Development and Scale-Up of a Commercial Fed Batch Refolding Process for an Anti-CD22 Two Chain Immunotoxin", Biotechnology Progress, 2014, vol. 30, No. 6, pp. 1380-1389.
International Search Report and Written Opinion for PCT/US2013/076625 dated Jul. 11, 2014, pp. 1-14.
International Preliminary Report on Patentability for PCT/US2013/076625 dated Jul. 2, 2015, pp. 1-10.
European Supplementary Search Report for European Patent Application No. 13863999.2 dated Jun. 22, 2016, pp. 1-3.

* cited by examiner

Primary Examiner — Julie Wu

(57) ABSTRACT

The present invention provides methods of preparing active immunoconjugates, including anti-CD22 immunoconjugates. Suitably, the methods include a fed-batch refolding process and/or column stripping process that result in an increase in yield of the immunoconjugate over other processes that do not utilize the methods.

19 Claims, 19 Drawing Sheets

METHODS OF PRODUCING IMMUNOCONJUGATES

CROSS-REFERENCE TO RELATED APPLICATIONS

This application is a U.S. National Stage application of International Application No. PCT/US2013/076625, filed on Dec. 19, 2013, said International Application No. PCT/US2013/076625 claims benefit under 35 U.S.C. § 119(e) of U.S. Provisional Application No. 61/740,111, filed on Dec. 20, 2012. Each of the above listed applications is incorporated by reference herein in its entirety for all purposes.

REFERENCE TO THE SEQUENCE LISTING

This application incorporates by reference a Sequence Listing submitted with this application as text file entitled MOXE-302US1_SEQ, created on Jun. 1, 2015, and having a size of 40 kilobytes.

BACKGROUND OF THE INVENTION

Field of the Invention

The present invention provides methods of preparing active immunoconjugates, including anti-CD22 immunoconjugates. Suitably, the methods include a fed-batch process and/or column elution process that result in an increase in yield of the immunoconjugate over other processes that do not utilize the methods.

Background Art

The large-scale, economic purification of proteins is a critical factor in production in the biopharmaceutical industry. Therapeutic proteins are typically produced using prokaryotic or eukaryotic cell lines that are engineered to express the protein of interest from a recombinant plasmid containing the gene encoding the protein. Separation of the desired protein from the mixture of components fed to the cells and cellular by-products to an adequate purity, e.g., sufficient for use as a human therapeutic, poses a formidable challenge to biologics manufacturers for several reasons.

Manufacturers of protein-based pharmaceutical products must comply with strict regulatory standards, including extremely stringent purity requirements. To ensure safety, regulatory agencies, such as Food and Drug Administration (FDA), require that protein-based pharmaceutical products are substantially free from impurities, including both product related contaminants such as aggregates, fragments and variants of the recombinant protein and process related contaminants such as host cell proteins, media components, viruses, DNA and endotoxins. While various protein purification schemes are available and widely used in the biopharmaceutical industry, they typically include an affinity-purification step, such as Protein A purification in the case of antibodies, in order to reach a pharmaceutically acceptable degree of purity.

The development of a purification scheme applicable to both a particular biomolecule and various biomolecules that is scaleable, controllable, and provides for high yield of a purified biomolecule, will allow its integration into product development at a very early stage in overall drug development. Therefore, it is desirable and advantageous to provide a simple and efficient process that can produce a drug substance of high quality and safety.

BRIEF SUMMARY OF THE INVENTION

In one embodiment methods of preparing an active immunoconjugate are provided. Suitably the immunoconjugate is deamidated at one or more residues, and the deamidation results in an inhibition of potency of the immunoconjugate. Suitably the methods comprise refolding the immunoconjugate in a fed-batch process and purifying the refolded immunoconjugate on one or more chromatography columns.

In further embodiments of preparing an active immunoconjugate, wherein said immunoconjugate is deamidated at one or more residues, and wherein said deamidation results in an inhibition of potency of said immunoconjugate, the method comprising refolding said immunoconjugate and purifying the refolded immunoconjugate using a two cycle elution on an ion exchange column, wherein the column is stripped between a first elution and a second elution with a stripping buffer comprising ethanolamine, arginine, Ethylenediaminetetraacetic acid (EDTA), urea and dithiothreitol (DTT).

In embodiments of the methods, refolding the immunoconjugate comprises a refold buffer having a pH 9.5 or less.

Suitably, the immunoconjugate comprises an antibody or antigen binding fragment thereof, for example an antibody or antigen binding fragment comprises a Fab, a Fab', a F(ab')2, a Fd, a single chain Fv or scFv, a disulfide linked Fv, a V-NAR domain, an IgNar, an intrabody, an IgGΔCH2, a minibody, a F(ab')3 a tetrabody, a triabody, a diabody, a single-domain antibody, DVD-Ig, Fcab, mAb2, a (scFv)2, or a scFv-Fc.

In exemplary embodiments, the antibody or antigen binding fragment binds a cell surface receptor, suitably CD22.

Suitably the immunoconjugate comprises a toxin, for example, toxins including, but not limited to, Pseudomonas exotoxin, ricin, abrin, diphtheria toxin and subunits thereof, as well as botulinum toxins A through F and variants, and derivatives thereof.

In exemplary embodiments, the toxin is Pseudomonas exotoxin, or variant thereof, suitably having an amino acid sequence selected from the group consisting of SEQ ID NOs: 16-22.

In embodiments, the antibody or antigen binding fragment thereof comprises a VH and a VL sequence, suitably the VH sequence is selected from the group consisting of SEQ ID NOs: 6-11, and the VL sequence is selected from the group consisting of SEQ ID NOs: 2, and 12-15.

In exemplary embodiments, the immunoconjugate comprises an anti-CD22 antibody or antigen binding fragment thereof and a PE or variant thereof, suitably the immunoconjugate is the Moxetumomab pasudotox immunotoxin comprising the VH-PE38 subunit of SEQ ID NO: 1 and the VL subunit of SEQ ID NO:2.

In embodiments, the refold buffer has a pH of 9.4.

In suitable embodiments, the fed batch process uses an addition rate of about 52 mL of solubilized inclusion bodies per L of refold buffer per hour to about 13 mL solubilized inclusion bodies per L refold buffer per hour, more suitably an addition rate of about 35 mL of solubilized inclusion bodies per L of refold buffer per hour to about 17 mL solubilized inclusion bodies per L refold buffer per hour, or an addition rate of about 30 mL of solubilized inclusion bodies per L of refold buffer per hour to about 18 mL solubilized inclusion bodies per L refold buffer per hour, or an addition rate of about 26 mL of solubilized inclusion bodies per L of refold buffer per hour.

Suitably, the stripping buffer for use in the various methods comprises about 30-60 mM ethanolamine, about 0.25 to about 0.75 M arginine, about 1-3 mM EDTA, about 7-9 M urea and about 9-11 mM DTT.

Also provided are compositions comprising an immunoconjugate having less than between about 25% and about 1% deamidated species, wherein the immunoconjugate is prepared by the various methods disclosed herein.

Also provided herein are methods of preparing an active immunoconjugate, wherein the immunoconjugate is deamidated at one or more residues, and wherein the deamidation results in an inhibition of potency of said immunoconjugate. Suitably, the method comprises refolding the immunoconjugate in a fed-batch process in a refold buffer having a pH of 9.5 or less, and purifying the refolded immunoconjugate using a two cycle elution on an ion exchange column, wherein the column is stripped between a first elution and a second elution with a stripping buffer comprising ethanolamine, arginine, Ethylenediaminetetraacetic acid (EDTA), urea and dithiothreitol (DTT).

Suitably, an amount of the immunoconjugate recovered from the method of preparation is at least three-hundred % (300%) greater than an amount of the immunoconjugate recovered utilizing a method that does not comprise a fed-batch refolding process and/or a two cycle elution on an ion exchange column that has been stripped using the stripping buffer.

Further embodiments, features, and advantages of the embodiments, as well as the structure and operation of the various embodiments, are described in detail below with reference to accompanying drawings.

BRIEF DESCRIPTIONS OF THE DRAWINGS

FIG. 1. shows a suitable renaturation and purification process flow for Moxetumomab pasudotox as described herein.

DETAILED DESCRIPTION OF THE INVENTION

Figure 1:
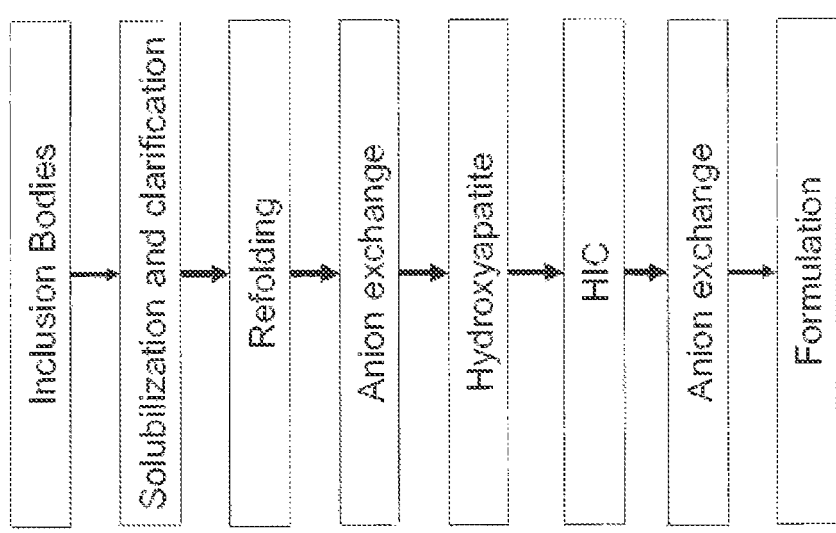
Figure 2:
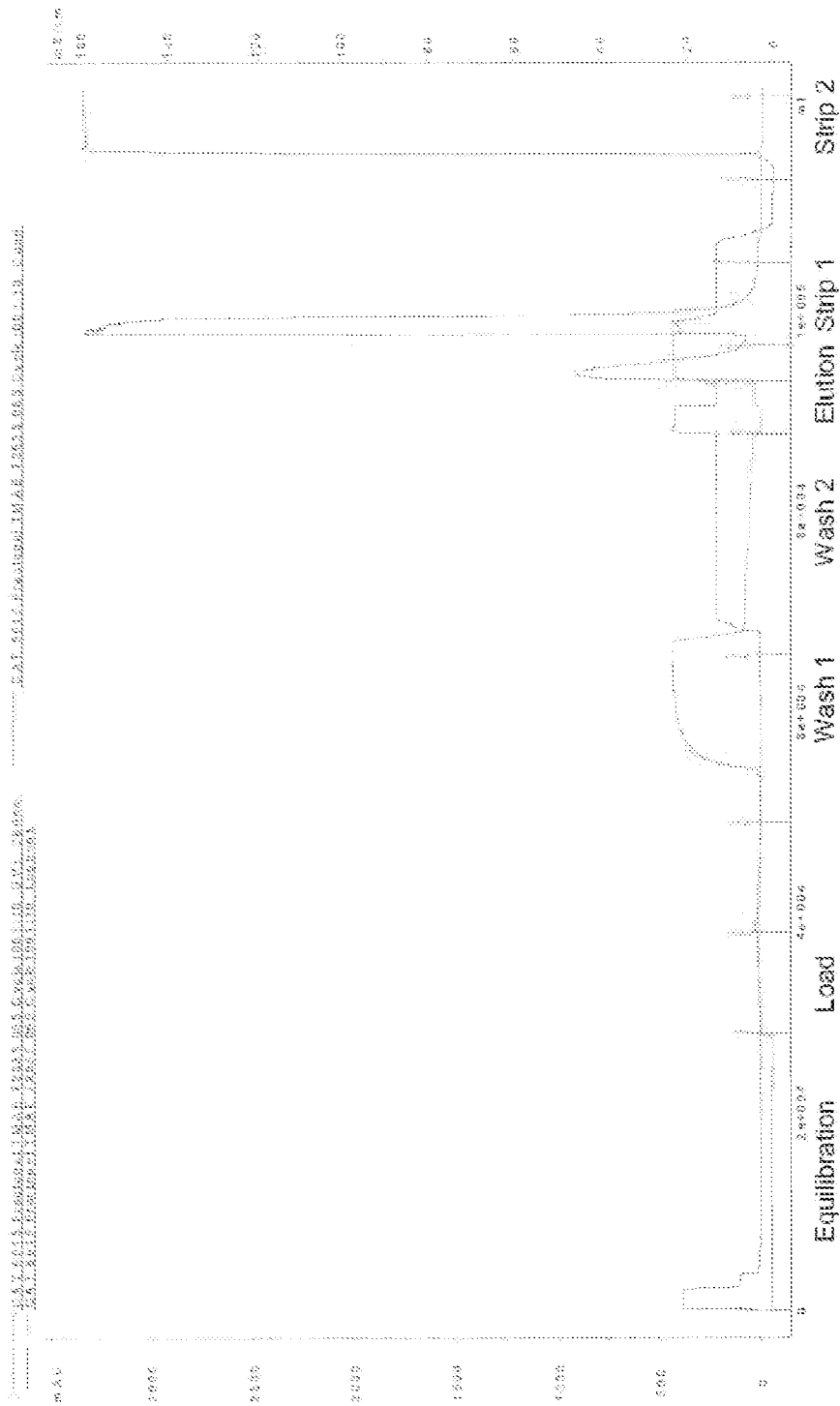
FIG. 2 shows the results of a Fractogel TMAE (M) capture step (Cycle 1).

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of ordinary skill in the art to which the present application pertains, unless otherwise defined. Reference is made herein to various methodologies and materials known to those of skill in the art. Standard reference works setting forth the general principles of recombinant DNA technology include Sambrook et al., "Molecular Cloning: A Laboratory Manual," 2nd Ed., Cold Spring Harbor Laboratory Press, New York (1989); Kaufman et al., Eds., "Handbook of Molecular and Cellular Methods in Biology in Medicine," CRC Press, Boca Raton (1995); and McPherson, Ed., "Directed Mutagenesis: A Practical Approach," IRL Press, Oxford (1991), the disclosures of each of which are incorporated by reference herein in their entireties.

The terms "polypeptide," "peptide," "protein," and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine Amino acid analogs refer to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions similarly to a naturally occurring amino acid. Negatively charged amino acids include aspartic acid (or aspartate) and glutamic acid (or glutamate). Positively charged amino acids include arginine, histidine, and lysine.

The "composition" to be purified herein comprises the polypeptide of interest and one or more impurities. The composition may be "partially purified" (i.e., having been subjected to one or more purification steps, or may be obtained directly from a host cell or organism producing the polypeptide (e.g., the composition may comprise harvested cell culture fluid).

An "acidic variant" is a variant of a polypeptide or immunoconjugate which is more acidic (e.g., as determined by cation exchange chromatography) than the polypeptide of interest. An example of an acidic variant is a deamidated variant. Deamidated proteins are those that have had some or all of the free amide functional groups hydrolyzed to carboxylic acids, such as conversion of glutamines to glutamic acid. The rate of this reaction is dependent on the primary sequence, three-dimensional structure, pH, temperature, buffer type, ionic strength and other solution properties. Importantly, the deamidation reaction introduces a negative charge into the molecule. As described further below, the protein deamidation can have a negative impact on protein activity.

As used herein, the terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and antibody fragments as described herein. The term "bispecific antibody" is intended to include any antibody that has two different binding specificities, i.e., the antibody binds two different epitopes, which can be located on the same target antigen or, more commonly, on different target antigens.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 186, 651-66, 1985); Novotny and Haber, *Proc. Natl. Acad. Sci. USA* 82, 4592-4596 (1985)). Five human immunoglobulin classes are defined on the basis of their heavy chain composition, and are named IgG, IgM, IgA, IgE, and IgD. The IgG-class and IgA-class antibodies are further divided into subclasses, namely, IgG1, IgG2, IgG3, and IgG4, and IgA1 and IgA2. The heavy chains in IgG, IgA, and IgD antibodies have three constant region domains, that are designated CHI, CH2, and CH3, and the heavy chains in IgM and IgE antibodies have four constant region domains, CHI, CH2, CH3, and CH4. Thus, heavy chains have one variable region and three or four constant regions Immunoglobulin structure and function are reviewed, for example, in Harlow et al., Eds., Antibodies: A Laboratory Manual, Chapter 14, Cold Spring Harbor Laboratory, Cold Spring Harbor (1988).

The term "antibody fragment" refers to a portion of an intact antibody and refers to the antigenic determining variable regions of an intact antibody. Examples of antibody fragments include, but are not limited to Fab, Fab', F(ab')2, Fv and single chain Fv fragments, linear antibodies, single chain antibodies, and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific and bind a single antigen. Furthermore, in contrast to polyclonal antibody preparations that typically include different antibodies directed against different determinants (epitopes), each monoclonal antibody is directed against a single determinant on the antigen. That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means, for instance, that an antibody binds to a protein with a $K_D$ of at least about 0.1 mM, but more usually at least about 1 μM. "Selectively binds" or "specifically binds" means at times that an antibody binds to a protein at times with a $K_D$ of at least about 0.1 mM or better, and at other times at least about 0.01 mM or better. Because of the sequence identity between homologous proteins in different species, specific binding can include an antibody that recognizes a tumor cell marker protein in more than one species.

The antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 57:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all, or substantially all, of the FRs are those of a human immunoglobulin sequence. The humanized antibody optionally will also comprise at least a portion of an immunoglobulin constant region (Fc), typically that of a human immunoglobulin. For further details, see Jones et al., *Nature* 327:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 7: 105-115 (1998); Harris, *Biochem. Soc. Transactions* 23: 1035-1038 (1995); Hurle and Gross, *Curr. Op. Biotech.* 5:428-433 (1994).

A "human antibody" is one that possesses an amino acid sequence that corresponds to that of an antibody produced by a human and/or has been made using any of the techniques for making human antibodies as disclosed herein. This definition of a human antibody specifically excludes a humanized antibody comprising non-human antigen-binding residues.

The term "immunoconjugate" or "conjugate" or "immunotoxin" as used herein refers to a compound or a derivative thereof that is linked to a cell binding agent (e.g., an anti-CD22 antibody or fragment thereof) and is defined by a generic formula: C-L-A, wherein C=cytotoxin, L=linker, and A=cell binding agent (e.g., anti-CD22 antibody or antibody fragment) Immunoconjugates can also be defined by the generic formula in reverse order: A-L-C.

The term "cytotoxin" or "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Examples of cytotoxic agents include, but are not limited to, abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain 1a of PE or the B chain of DT) and replacing it with a different targeting moiety, such as an antibody.

In some embodiments, the toxin is *Pseudomonas* exotoxin. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

A "PE immunoconjugate" or "PE immunotoxin" is an immunoconjugate or immunotoxin comprising an antibody or antigen binding fragment thereof and a PE toxin or variant thereof.

By "purifying" a polypeptide or immunoconjugate from a composition comprising the polypeptide and one or more impurities, is meant increasing the degree of purity of the polypeptide in the composition by removing (completely or partially) at least one impurity from the composition. According to the present invention, purification is performed without the use of an affinity chromatography step.

The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "ion-exchange" and "ion-exchange chromatography" refers to the chromatographic process in which a solute of interest (such as a protein) in a mixture interacts with a charged compound linked (such as by covalent attachment) to a solid phase ion exchange material such that the solute of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode chromatography.

The phrase "ion exchange material" refers to a solid phase that is negatively charged (i.e., a cation exchange resin) or positively charged (i.e., an anion exchange resin). The charge may be provided by attaching one or more charged ligands to the solid phase, e.g., by covalent linking. Alternatively, or in addition, the charge may be an inherent property of the solid phase (e.g., as is the case for silica, which has an overall negative charge).

An "anion exchange resin" refers to a solid phase which is positively charged, thus having one or more positively charged ligands attached thereto. Any positively charged ligand attached to the solid phase suitable to form the anionic exchange resin can be used, such as quaternary amino groups Commercially available anion exchange resins include DEAE cellulose, Poros PI 20, PI 50, HQ 10, HQ 20, HQ 50, D 50 from Applied Biosystems, Sartobind Q from Sartorius, MonoQ, MiniQ, Source 15Q and 30Q, Q, DEAE and ANX Sepharose Fast Flow, Q Sepharose High Performance, QAE SEPHADEX™ and FAST Q SEPHAROSE™ (GE Healthcare), WP PEI, WP DEAM, WP QUAT from J. T. Baker, Hydrocell DEAE and Hydrocell QA from Biochrom Labs Inc., U Osphere Q, Macro-Prep DEAE and Macro-Prep High Q from Biorad, Ceramic HyperD Q, ceramic HyperD DEAE, Trisacryl M and LS DEAE, Spherodex LS DEAE, QMA Spherosil LS, QMA Spherosil M and Mustang Q from Pall Technologies, DOWEX Fine Mesh Strong Base Type I and Type II Anion Resins and DOWEX MONOSPHER E 77, weak base anion from Dow Liquid Separations, Intercept Q membrane, Matrex Cellufine A200, A500, Q500, and Q800, from Millipore, Fractogel EMD TMAE, Fractogel EMD DEAE and Fractogel EMD DMAE from EMD, Amberlite weak strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman.

By "solid phase" is meant a non-aqueous matrix to which one or more charged ligands can adhere. The solid phase may be a purification column, a discontinuous phase of discrete particles, a membrane, or filter etc. Examples of materials for forming the solid phase include polysaccharides (such as agarose and cellulose); and other mechanically stable matrices such as silica (e.g., controlled pore glass), poly(styrenedivinyl)benzene, polyacrylamide, ceramic particles and derivatives of any of the above.

The term "specific binding" as used herein, such as to describe interactions between a molecule of interest and a ligand bound to a solid phase matrix, refers to the generally reversible binding of a protein of interest to a ligand through the combined effects of spatial complementarity of protein and ligand structures at a binding site coupled with electrostatic forces, hydrogen bonding, hydrophobic forces, and/or van der Waals forces at the binding site. The greater the spatial complementarity and the stronger the other forces at the binding site, the greater will be the binding specificity of a protein for its respective ligand. Non-limiting examples of specific binding include antibody-antigen binding, enzyme-substrate binding, enzyme-cofactor binding, metal ion chelation, DNA binding protein-DNA binding, regulatory protein-protein interactions, and the like.

The term "non-specific binding" as used herein, such as to describe interactions between a molecule of interest and a ligand or other compound bound to a solid phase matrix, refers to binding of a protein of interest to the ligand or compound on a solid phase matrix through electrostatic forces, hydrogen bonding, hydrophobic forces, and/or van der Waals forces at an interaction site, but lacking structural complementarity that enhances the effects of the non-structural forces. Examples of non-specific interactions include, but are not limited to, electrostatic, hydrophobic, and van der Waals forces as well as hydrogen bonding.

A "buffer" used in the present invention is a solution that resists changes in pH by the addition of acid or base by the action of its acid-base conjugates components. Various buffers can be employed in a method of the present invention depending on the desired pH of the buffer and the particular step in the purification process [see Buffers. A Guide for the Preparation and Use of Buffers in Biological Systems, Gueffroy, D., ed. Calbiochem Corporation (1975)]. Non-limiting examples of buffer components that can be used to control the pH range desirable for a method of the invention include acetate, citrate, histidine, phosphate, ammonium buffers such as ammonium acetate, succinate, MES, CHAPS, MOPS, MOPSO, HEPES, Tris, and the like, as well as combinations of these TRIS-malic acid-NaOH, maleate, chloroacetate, formate, benzoate, propionate, pyridine, piperazine, ADA, PIPES, ACES, BES, TES, tricine, bicine, TAPS, ethanolamine, CHES, CAPS, methylamine, piperidine, O-boric acid, carbonic acid, lactic acid, butaneandioic acid, diethylmalonic acid, glycylglycine, HEPPS, HEPPSO, imidazole, phenol, POPSO, succinate, TAPS, amine-based, benzylamine, trimethyl or dimethyl or ethyl or phenyl amine, ethylenediamine, or mopholine Additional components (additives) can be present in a buffer as needed, e.g., salts can be used to adjust buffer ionic strength, such as sodium chloride, sodium sulfate and potassium chloride; and other additives such as amino acids (such as glycine and histidine), chaotropes (such as urea), alcohols (such as ethanol, mannitol, glycerol, and benzyl alcohol), detergents (see supra.), and sugars (such as sucrose, mannitol, maltose, trehalose, glucose, and fructose). The buffer components and additives, and the concentrations used, can vary according to the type of chromatography practiced in the invention.

The "loading buffer" is that which is used to load the composition comprising the polypeptide molecule of interest and one or more impurities onto the ion exchange resin. The loading buffer has a conductivity and/or pH such that the polypeptide molecule of interest (and generally one or more impurities) is/are bound to the ion exchange resin or such that the protein of interest flows through the column while the impurities bind to the resin.

The term "wash buffer" when used herein refers to a buffer used to wash or re-equilibrate the ion exchange resin, prior to eluting the polypeptide molecule of interest. Conveniently, the wash buffer and loading buffer may be the same, but this is not required.

The "elution buffer" is used to elute the polypeptide of interest from the solid phase. The conductivity and/or pH of the elution buffer is/are such that the polypeptide of interest is eluted from the ion exchange resin.

The "pI" or "isoelectric point" of a polypeptide refer to the pH at which the polypeptide's positive charge balances its negative charge, pi can be calculated from the net charge of the amino acid residues or sialic acid residues of attached carbohydrates of the polypeptide or can be determined by isoelectric focusing.

By "binding" a molecule to an ion exchange material, is meant exposing the molecule to the ion exchange material under appropriate conditions (pH/conductivity) such that the molecule is reversibly immobilized in or on the ion exchange material by virtue of ionic interactions between the molecule and a charged group or charged groups of the ion exchange material.

By "washing" the ion exchange material is meant passing an appropriate buffer through or over the ion exchange material.

To "elute" a molecule (e.g., polypeptide or impurity) from an ion exchange material is meant to remove the molecule therefrom by altering the ionic strength of the buffer surrounding the ion exchange material such that the buffer competes with the molecule for the charged sites on the ion exchange material.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of and/or" consisting essentially of are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

*Pseudomonas* Exotoxin and Other Toxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diphtheria toxin is isolated from *Corynebaclerium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Bio-*

*chem. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:621-631 (1974) and U.S. Pat. No. 3,060, 165).

Abrin includes toxic lectins from *Abrus precalorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52: 1095 (1988); and Olsnes, *Methods Enzymol.* 50:330-335 (1978)).

In preferred embodiments of the present invention, the toxin is *Pseudomonas* exotoxin (PE). The *Pseudomonas* exotoxin (or exotoxin A) is an exotoxin produced by *Pseudomonas aeruginosa*. The term "*Pseudomonas* exotoxin" as used herein refers to a full-length native (naturally occurring) PE or a PE that has been modified. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:3) and REDL (SEQ ID NO:4). See Siegall, et al., *J. Biol. Chem.* 264: 14256-14261 (1989). In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The native PE sequence is provided in commonly assigned U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain b (amino acids 365-399) remains undefined, although a large part of it, amino acids 365-380, can be deleted without loss of cytotoxicity. See Siegall, et al., (1989), supra.

PE employed in the present invention includes the native sequence, cytotoxic fragments of the native sequence, and conservatively modified variants of native PE and its cytotoxic fragments. PE variants useful in the invention are described in U.S. Pat. No. 7,355,012, and WO 2007/016150 and WO 2009/032954, the disclosures of each of which are incorporated by reference herein in their entireties. Cytotoxic fragments of PE include those which are cytotoxic with or without subsequent proteolytic or other processing in the target cell (e.g., as a protein or pre-protein). Cytotoxic fragments of PE include PE40, PE38, and PE35.

In preferred embodiments, the PE has been modified to reduce or eliminate nonspecific cell binding, frequently by deleting domain Ia as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E.

PE40 is a truncated derivative of PE as previously described in the art, with a deletion of domain 1a of the native PE molecule. See, Pai, et al., *Proc. Nat'l Acad. Sci USA* 55:3358-62 (1991); and Kondo, et al., *J. Biol. Chem.* 263:9470-9475 (1988). PE35 is a 35 kD carboxyl-terminal fragment of PE in which amino acid residues 1-279 have been deleted and the molecule commences with a met at position 280 followed by amino acids 281-364 and 381-613 of native PE. PE35 and PE40 are disclosed, for example, in U.S. Pat. Nos. 5,602,095 and 4,892,827. PE4E is a form of PE where all of the domains of native PE are present, but where the basic residues of domain 1a at positions 57, 246, 247 and 249 are replaced with acidic residues (glutamine acid, or "E").

In some preferred embodiments, the cytotoxic fragment PE38 is employed. PE38 is a truncated PE pro-protein composed of amino acids 253-364 and 381-613 which is activated to its cytotoxic form upon processing within a cell (see e.g., U.S. Pat. Nos. 5,608,039, 7,355,012, and Pastan et al., *Biochim. Biophys. Acta* 1333:$C_1$-$C_6$ (1997), the disclosures of each of which are incorporated by reference herein in their entireties).

As noted above, some or all of domain 1b may be deleted, and the remaining portions joined by a linker or directly by a peptide bond. Some of the amino portion of domain II may be deleted. And, the C-terminal end may contain the native sequence of residues 609-613 (REDLK) (SEQ ID NO: 5), or may contain a variation found to maintain the ability of the construct to translocate into the cytosol, such as REDL (SEQ ID NO:4) or KDEL (SEQ ID NO:3), and repeats of these sequences. See, e.g., U.S. Pat. Nos. 5,854,044; 5,821,238; and 5,602,095 and WO 99/51643. While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

Anti-CD22/PE Immunoconjugates

In one embodiment, the polypeptide of interest comprises an antibody that specifically binds CD22. "CD22" refers to a lineage-restricted B cell antigen belonging to the Ig superfamily. It is expressed in 60-70% of B cell lymphomas and leukemias and is not present on the cell surface in early stages of B cell development or on stem cells. See, e.g., Vaickus et al., *Crit. Rev. Oncol/Hematol*. 77:267-297 (1991). In another embodiment, the polypeptide of interest is an antibody fragment that binds CD22 (e.g., Fab, or scFv).

As used herein, the term "anti-CD22" in reference to an antibody, refers to an antibody that specifically binds CD22 and includes reference to an antibody which is generated against CD22. In some embodiments, the CD22 is a primate CD22 such as human CD22. In one embodiment, the antibody is generated against human CD22 synthesized by a non-primate mammal after introduction into the animal of cDNA which encodes human CD22. In a further embodiment, the polypeptide of interest is a CD22 antibody immunoconjugate that comprises the PE38 exotoxin.

One example of a CD22/PE38 immunoconjugate is Moxetumomab pasudotox described in International Patent Application Publication Nos. WO 2012/015912, WO 98/41641 and WO2003/27135, U.S. Pat. Nos. 7,541,034, 7,355,012, and U.S. Publication No. 2007/0189962, all of which are herein incorporated by reference in their entireties. Moxetumomab pasudotox (CAT-8015) is a recombinant immunotoxin protein composed of an antibody Fv fragment based on the murine anti-CD22 antibody RFB4 fused to a truncated form of the *Pseudomonas* exotoxin protein, PE38. The anti-CD22 Fv fragment consists of two domains, a VL and a VH, where the latter was modified to improve binding to the human CD22 target. The Moxetumomab pasudotox protein is comprised of two independent polypeptides, the VL chain (SEQ ID NO:2), and the VH chain, fused at the C-terminus to the PE38 domain (VH-PE38) (SEQ ID NO: 1). Other VL and VH-PE38 sequences useful in this invention are described in U.S. Pat. Nos. 7,541,034, 7,355,012, 2007/0189962 and WO 2012/015912, the disclosures of each of which are incorporated by reference herein in their entireties. Both domains were designed to each contain engineered cysteine residues that permit formation of an intermolecular disulfide bond. This feature increases the stability of the fusion protein.

The amino acid sequence of the VH-P38 Subunit (SEQ ID NO: 1) of Moxetumomab pasudotox is the following:

(SEQ ID NO: 1)
MEVQLVESGGGLVKPGGSLKLSCAASGFAFSIYDMSWVRQTPEKCLEWVA

YISSGGGTTYYPDTVKGRFTISRDNAKNTLYLQMSSLKSEDTAMYYCARH

SGYGTHWGVLFAYWGQGTLVSA<u>KASGG</u>PEGGSLAALTAHQACHLPLETFT

RHRQPRGWEQLEQCGYPVQRLVALYIAARLSWNQVDQVIRALASPGSGGD

LGEAIREQPEQARLALTLAAAESERFVRQGTGNDEAGAANGPADSGDALL

ERNYPTGAEFLGDGGDVSFSTRGTQNWTVERLLQAHRQLEERGYVFVGYH

GTFLEAAQSIVFGGVRARSQDLDAIWRGFYIAGDPALAYGYAQDQEPDAR

GRIRNGALLRVYVPRSSLPGFYRTSLTLAAPEAAGEVERLIGHPLPLRLD

AITGPEEEGGRLETILGWPLAERTWIPSAIPTDPRNVGGDLDPSSIPDKE

QAISALPDYASQPGKPPREDLK

The PE38 sequence is shown in bold, and the five amino acid linker between the VH domain and the PE38 domain is shown underlined.

The amino acid sequence of the VL Subunit (SEQ ID NO:2) of Moxetumomab pasudotox is the following:

(SEQ ID NO: 2)
MDIQMTQTTSSLSASLGDRVTISCRASQDISNYLNWYQQKPDGTVKLLIY

YTSILHSGVPSRFSGSGSGTDYSLTISNLEQEDFATYFCQQGNTLPWTFG

CGTKLEIK

In further embodiments, the amino acid sequence of the VH domain of the immunoconjugate is one of the following:

(SEQ ID NO: 6)
MEVQLVESGGGLVKPGGSLKLSCAASGFAFSIYDMSWVRQTPEKCLEWVA

YISSGGGTTYYPDTVKGRFTISRDNAKNTLYLQMSSLKSEDTAMYYCARH

SGYGTHWGVLFAYWGQGTLVTVSA (SEQ ID NO: 7)
MEVQLVESGGGLVKPGGSLKLSCAASGFAFSIYDMSWVRQTPEKCLEWVA

YISSGGGTTYYPDTVKGRFTISRDNAKNTLYLQMSSLKSEDTAMYYCARH

SGYGYNWGVLFAYWGQGTLVTVSA (SEQ ID NO: 8)
MEVQLVESGGGLVKPGGSLKLSCAASGFAFSIYDMSWVRQTPEKCLEWVA

YISSGGGTTYYPDTVKGRFTISRDNAKNTLYLQMSSLKSEDTAMYYCARH

SGYGTTWGVLFAYWGQGTLVTVSA (SEQ ID NO: 9)
MEVQLVESGGGLVKPGGSLKLSCAASGFAFSIYDMSWVRQTPEKCLEWVA

YISSGGGTTYYPDTVKGRFTISRDNAKNTLYLQMSSLKSEDTAMYYCARH

SGYGSTYGVLFAYWGQGTLVTVSA (SEQ ID NO: 10)
MEVQLVESGGGLVKPGGSLKLSCAASGFAFSIYDMSWVRQTPEKCLEWVA

YISSGGGTTYYPDTVKGRFTISRDNAKNTLYLQMSSLKSEDTAMYYCARH

SGYGTHWGVLFAYWGQGTLVTVSA (SEQ ID NO: 11)
MEVQLVESGGGLVKPGGSLKLSCAASGFAFSIYDMSWVRQTPEKCLEWVA

YISSGGGTTYYPDTVKGRFTISRDNAKNTLYLQMSSLKSEDTAMYYCARH

SGYGSSYGVLFAYWGQGTLVTVSA

In additional embodiments, the amino acid sequence of the VL domain of the immunoconjugate is one of the following:

(SEQ ID NO: 12)
MDIQMTQTTSSLSASLGDRVTISCRASQDIARYLNWYQQKPDGTVKLLIY

YTSILHSGVPSRFSGSGSGTDYSLTISNLEQEDFATYFCQQGNTLPWTFG

CGTKLEIK (SEQ ID NO: 13)
MDIQMTQTTSSLSASLGDRVTISCRASQDIHGYLNWYQQKPDGTVKLLIY

YTSILHSGVPSRFSGSGSGTDYSLTISNLEQEDFATYFCQQGNTLPWTFG

CGTKLEIK (SEQ ID NO: 14)
MDIQMTQTTSSLSASLGDRVTISCRASQDIGRYLNWYQQKPDGTVKLLIY

YTSILHSGVPSRFSGSGSGTDYSLTISNLEQEDFATYFCQQGNTLPWTFG

CGTKLEIK (SEQ ID NO: 15)
MDIQMTQTTSSLSASLGDRVTISCRASQDIRGYLNWYQQKPDGTVKLLIY

YTSILHSGVPSRFSGSGSGTDYSLTISNLEQEDFATYFCQQGNTLPWTFG

CGTKLEIK

In certain other embodiments, the PE toxin of the immunoconjugate is a PE or variant thereof selected from the following:

Native PE
(SEQ ID NO: 16)
AEEAFDLWNECAKACVLDLKDGVRSSRMSVDPAIADTNGQGVLHYSMVLE

GGNDALKLAIDNALSITSDGLTIRLEGGVEPNKPVRYSYTRQARGSWSLN

WLVPIGHEKPSNIKVFIHELNAGNQLSHMSPIYTIEMGDELLAKLARDAT

FFVRAHESNEMQPTLAISHAGVSWMAQTQPRREKRWSEWASGKVLCLLDP

LDGVYNYLAQQRCNLDDTWEGKIYRVLAGNPAKHDLDIKPTVISHRLHFP

EGGSLAALTAHQACHLPLETFTRHRQPRGWEQLEQCGYPVQRLVALYLAA

RLSWNQVDQVIRNALASPGSGGDLGEAIREQPEQARLALTLAAAESERFV

RQGTGNDEAGAANGPADSGDALLERNYPTGAEFLGDGGDVSFSTRGTQNW

TVERLLQAHRQLEERGYVFVGYHGTFLEAAQSIVFGGVRARSQDLDAIWR

GFYIAGDPALAYGYAQDQEPDARGRIRNGALLRVYVPRSSLPGFYRTSLT

LAAPEAAGEVERLIGHPLPLRLDAITGPEEEGGRLETILGWPLAERTWIP

SAIPTDPRNVGGDLDPSSIPDKEQAISALPDYASQPGKPPREDLK

PE40
(SEQ ID NO: 17)
GGSLAALTAHQACHLPLETFTRHRQPRGWEQLEQCGYPVQRLVALYLAAR

LSWNQVDQVIRNALASPGSGGDLGEAIREQPEQARLALTLAAAESERFVR

QGTGNDEAGAANADVVSLTCPVAAGECAGPADSGDALLERNYPTGAEFLG

DGGDVSFSTRGTQNWTVERLLQAHRQLEERGYVFVGYHGTFLEAAQSIVF

GGVRARSQDLDAIWRGFYIAGDPALAYGYAQDQEPDARGRIRNGALLRVY

VPRSSLPGFYRTSLTLAAPEAAGEVERLIGHPLPLRLDAITGPEEEGGRL

ETILGWPLAERTVVIPSAIPTDPRNVGGDLDPSSIPDKEQAISALPDYAS

QPGKPPREDLK

PE38
(SEQ ID NO: 18)
GGSLAALTAHQACHLPLETFTRHRQPRGWEQLEQCGYPVQRLVALYLAAR

LSWNQVDQVIRNALASPGSGGDLGEAIREQPEQARLALTLAAAESERFVR

QGTGNDEAGAANGPADSGDALLERNYPTGAEFLGDGGDVSFSTRGTQNWT

VERLLQAHRQLEERGYVFVGYHGTFLEAAQSIVFGGVRARSQDLDAIWRG

FYIAGDPALAYGYAQDQEPDARGRIRNGALLRVYVPRSSLPGFYRTSLTL

AAPEAAGEVERLIGHPLPLRLDAITGPEEEGGRLETILGWPLAERTWIPS

AIPTDPRNVGGDLDPSSIPDKEQAISALPDYASQPGKPPREDLK

PE35
(SEQ ID NO: 19)
MWEQLEQCGYPVQRLVALYLAARLSWNQVDQVIRNALASPGSGGDLGEAI

REQPEQARLALTLAAAESERFVRQGTGNDEAGAANGPADSGDALLERNYP

TGAEFLGDGGDVSFSTRGTQNWTVERLLQAHRQLEERGYVFVGYHGTFLE

AAQSIVFGGVRARSQDLDAIWRGFYIAGDPALAYGYAQDQEPDARGRIRN

GALLRVYVPRSSLPGFYRTSLTLAAPEAAGEVERLIGHPLPLRLDAITGP

EEEGGRLETILGWPLAERTVVIPSAIPTDPRNVGGDLDPSSIPDKEQAIS

ALPDYASQPGKPPREDLK

PE-LR
(SEQ ID NO: 20)
RHRQPRGWEQLPTGAEFLGDGGDVSFSTRGTQNWTVERLLQAHRQLEERG

YVFVGYHGTFLEAAQSIVFGGVRARSQDLDAIWRGFYIAGDPALAYGYAQ

DQEPDARGRIRNGALLRVYVPRSSLPGFYRTSLTLAAPEAAGEVERLIGH

PLPLRLDAITGPEEEGGRLETILGWPLAERTVVIPSAIPTDPRNVGGDLD

PSSIPDKEQAISALPDYASQPGKPPREDLK

PE-LR-6X
(SEQ ID NO: 21)
RHRQPRGWEQLPTGAEFLGDGGDVSFSTRGTQNWTVERLLQAHRQLEEGG

YVFVGYHGTFLEAAQSIVFGGVRARSQDLDAIWAGFYIAGDPALAYGYAQ

DQEPDAAGRIRNGALLRVYVPRSSLPGFYATSLTLAAPEAAGEVERLIGH

PLPLRLDAITGPEEAGGRLETILGWPLAERTVVIPSAIPTDPRNVGGDLD

PSSIPDSEQAISALPDYASQPGKPPREDLK

PE-38 (Moxetumomab pasudotox)
(SEQ ID NO: 22)
PEGGSLAALTAHQACHLPLETFTRHRQPRGWEQLEQCGYPVQRLVALYLA

ARLSWNQVDQVIRNALASPGSGGDLGEAIREQPEQARLALTLAAAESERF

VRQGTGNDEAGAANGPADSGDALLERNYPTGAEFLGDGGDVSFSTRGTQN

WTVERLLQAHRQLEERGYVEVGYHGTFLEAAQSIVEGGVRARSQDLDAIW

-continued

RGFYIAGDPALAYGYAQDQEPDARGRIRNGALLRVYVPRSSLPGFYRTSL

TLAAPEAAGEVERLIGHPLPLRLDAITGPEEEGGRLETILGWPLAERTVV

IPSAIPTDPRNVGGDLDPSSIPDKEQAISALPDYASQPGKPPREDLK

The PE toxin of the immunoconjugate is fused or conjugated to either the VH or VL domain directly or via a linker at either the N-terminus or the C-terminus of the VH or VL domain. An example of a linker is described above for Moxetumomab pasudotox and corresponds to the amino acid sequence KASGG (SEQ ID NO: 23). Additional linkers can be readily generated by techniques known in the art.

Expression of a PE Immunoconjugate

The PE immunoconjugate of the present invention is suitably expressed in cells, such as bacterial cells, and then isolated from inclusion bodies. The PE immunoconjugate isolated from inclusion bodies is then further purified/isolated using downstream steps as described herein.

A variety of host-expression vector systems may be utilized to express the PE immunoconjugate of the present invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

DNA encoding each of the VL and VH-PE toxin (e.g., VH-PE38) polypeptides can be introduced into an expression vector by techniques well known in the art.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes vehicles for introducing the nucleic acid into a cell in vitro, ex vivo or in vivo. A large number of vectors known in the art may be used to manipulate nucleic acids, incorporate response elements and promoters, such as inducible promoters, into genes, etc. Possible vectors include, for example, plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini Such vectors may be engineered to contain selectable marker genes that provide for the selection of cells. Such markers allow identification and/or selection of host cells that express the proteins encoded by the marker.

The term "expression vector" refers to a vector, plasmid or vehicle designed to enable the expression of an inserted nucleic acid sequence following transformation into the host. The cloned gene, i.e., the inserted nucleic acid sequence, e.g., a gene encoding an anti-CD22 VH, anti-CD22 VL, or anti-CD22 VH or VL fused to a PE toxin, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; including, but are not limited to, the SV40 early (SV40) promoter region, the promoter contained in the 3' long terminal repeat (LTR) of Rous sarcoma virus (RSV), the EIA or major late promoter (MLP) of adenoviruses (Ad), the human cytomegalovirus (HCMV) immediate early promoter, the herpes simplex virus (HSV) thymidine kinase (TK) promoter, the baculovirus IE1 promoter, the elongation factor 1 alpha (EF1) promoter, the glyceraldehyde-3-phosphate dehydrogenase (GAPDH) promoter, the phosphoglycerate kinase (PGK) promoter, the ubiquitin C (Ubc) promoter, the albumin promoter, the regulatory sequences of the mouse metallothionein-L promoter and transcriptional control regions, the ubiquitous promoters (HPRT, vimentin, β-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters. In addition, these expression sequences may be modified by addition of enhancer or regulatory sequences and the like.

The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

The VL and VH-PE38 polypeptides are suitably expressed in cells, e.g., bacterial cells, such as *E. coli*. The polypeptides are expressed, e.g., in *E. coli* cells and isolated from inclusion bodies. In certain embodiments, the VL and VH-PE38 subunits are expressed in different cells. For example, the VL is expressed in one cell on a first vector and the VH-PE38 is expressed in a different cell on a second vector. In other embodiments, the VL and VH-PE38 subunits are expressed in the same cell on different vectors, for example, the VL is expressed in one cell on a first vector, and the VH-PE38 is expressed in the same cell on a different vector. In certain other embodiments, the VL and VH-PE38 subunits are expressed on the same vector in the same cell. Inclusion bodies from the cells are recovered, solubilized and the VL and VH-PE38 subunits combined to form an immunoconjugate, as described herein.

Methods of Preparing Immunoconjugates

In embodiments, provided herein are methods of preparing active immunoconjugates, i.e., immunoconjugates capable of binding a desired target and delivering the compound (e.g., immunotoxin) that is attached to the cell targeting agent (e.g., an antibody, antibody fragment or other protein).

The methods described herein are suitably used to prepare immunoconjugates that are deamidated at one or more residues. As described herein, such deamidation often results in an inhibition of potency of an immunoconjugate, and thus the methods provided are beneficial to preparing active immunoconjugates suitable for clinical settings.

As described herein, immunoconjugates are suitably prepared using expression systems from bacteria, including *E. coli*. Inclusion bodies from the cells are recovered, solubilized and the proteins are recovered. In embodiments, the VL and VH-toxin subunits designed to form an immunoconjugate, as described herein, are prepared in the bacterial cells.

As described herein, inclusion bodies comprising the desired immunoconjugate subunits are solubilized, concentrated and clarified. Suitable methods of clarification are described herein as well as in the disclosure and examples of WO2012/015912, the disclosure of which is incorporated by reference herein in its entirety. Following clarification, refolding of the immunoconjugate is carried out.

In embodiments, methods of preparing immunoconjugates suitably comprise refolding an immunoconjugate using a fed-batch process. Following the refolding, the refolded immunoconjugate is purified with one or more chromatography columns as described herein as well as in WO2012/015912.

As used herein "refolding" refers to the process under which a protein, isolated from inclusion bodies, is folded into its characteristic and functional three-dimensional structure from a prior random orientation.

A "fed-batch" process refers to a refolding process in which a solubilized inclusion body mixture (containing the desired immunoconjugate) is added (i.e., injected or mixed) to a suitable refold buffer at a controlled rate over a period of time. Suitably, the addition occurs at a steady rate over the entire time course, though the rate can also be varied during the process if desired. This addition time course is referred to herein as the "addition rate," and suitably is expressed in L/hr.

It has been unexpectedly discovered that the use of a fed-batch process in which the subunits of an immunoconjugate are initially present at a low concentration, and the concentration is then increased over a relatively extended period of time (suitably at a fixed addition rate over the course of 2, 3, 4, 5, 6 hours, etc.), results in an increased yield of the immunoconjugate in comparison to non-fed-batch processes that utilizes a bulk addition of subunits, in which the concentration is initially higher and does not change with time. This discovery is particularly surprising when utilizing the VL and VH-PE38 subunits described herein which must refold together (i.e., come together in a dilute solution) in order to form the final immunoconjugate, in contrast to a single component protein.

In exemplary embodiments, the yield of recovered immunoconjugate is suitably at least about 20% greater, at least about 30% greater, at least about 40% greater, at least about 50% greater, at least about 60% greater, at least about 70% greater, at least about 80% greater, at least about 90% greater, at least about 100% greater, at least about 125% greater, at least about 150% greater, at least about 175% greater, at least about 200% greater, at least about 300% greater, at least about 400% greater, at least about 500% greater, at least about 600% greater, at least about 700% greater, at least about 800% greater, at least about 900% greater, etc., in comparison to non-fed-batch processes that utilizes a bulk addition of subunits and a constant concentration of subunits.

In certain further embodiments, the yield of recovered immunoconjugate is suitably at least about 20% greater, at least about 30% greater, at least about 40% greater, at least about 50% greater, at least about 60% greater, at least about 70% greater, at least about 80% greater, at least about 90% greater, at least about 100% greater, at least about 125% greater, at least about 150% greater, at least about 175% greater, at least about 200% greater, at least about 300% greater, at least about 400% greater, at least about 500% greater, at least about 600% greater, at least about 700% greater, at least about 800% greater, at least about 900% greater, etc., wherein the immunoconjugate is refolded in a fed-batch process in a refold buffer having a pH of 9.5 or less. In further embodiments, the refolded immunoconjugate is purified using a two cycle elution on an ion exchange column, wherein the column is stripped between a first elution and a second elution with a stripping buffer comprising ethanolamine, arginine, Ethylendiaminetetraacetic acid (EDTA), urea and dithiothreitol (DTT). In other embodiments, the process of recovering said immunoconjugate corresponds to that of a non-fed batch process, except for having the refold performed in a fed-batch process in a refold buffer having a pH or 9.5 or less and/or purifying said immunoconjugate using a two cycle elution on an ion exchange column, wherein the column is stripped between a first elution and a second elution with a stripping buffer comprising ethanolamine, arginine, Ethylendiaminetetraacetic acid (EDTA), urea and dithiothreitol (DTT).

Suitably, the addition rate (L/hr) of the solubilized inclusion bodies is set so that a solubilized inclusion body mixture is added to a refold buffer (suitably pre-chilled) over the course of approximately 2-8 hours, suitably 3-6 hours, 3-5 hours, or more suitably over the course of about 4 hours.

In embodiments, the addition is over the course of 1-10 hours, using an addition rate of about 100 mL of solubilized inclusion bodies per L of refold buffer per hour to an addition rate of about 5 mL solubilized inclusion bodies per L refold buffer per hour is utilized (about 100 mL/L/hr to about 5 mL/L/hr). In exemplary embodiments, the addition is over the course of 2-8 hours, using an addition rate of about 52 mL of solubilized inclusion bodies per L of refold buffer per hour to an addition rate of about 13 mL solubilized inclusion bodies per L refold buffer per hour is utilized (about 52 mL/L/hr to about 13 mL/L/hr). In further embodiments, the addition is over the course of 3-6 hours, using an addition rate of about 35 mL solubilized inclusion bodies per L refold buffer per hour to an addition rate of about 17 mL solubilized inclusion bodies per L refold buffer per hour (about 35 mL/L/hr to about 17 mL/L/hr). In further embodiments, the addition is over the course of 3.5-5 hours, using an addition rate of about 30 mL solubilized inclusion bodies per L refold buffer per hour to an addition rate of about 18 mL solubilized inclusion bodies per L refold buffer per hour (about 30 mL/L/hr to about 18 mL/L/hr). In still further embodiments, the addition is over the course of about 4 hours, using an addition rate of about 26 mL solubilized inclusion bodies per L refold buffer per hour (about 26 mL/L/hr). In other embodiments, further addition rates can also be utilized in the fed-batch processes described herein.

Also provided are additional methods for preparing an immunoconjugate, wherein the immunoconjugate is deamidated at one or more residues, and wherein the deamidation results in an inhibition of potency of the immunoconjugate. Suitably the methods comprise refolding the immunoconjugate using any of the methods described herein or as disclosed in WO 2012/152912. The refolded immunoconjugate is then purified with a two-cycle elution on an ion exchange column.

As described herein, for column cleaning and reuse, suitably the column is stripped between operating cycles (i.e., column load, wash, elute) of the refolded immunoconjugate utilizing a stripping buffer. In exemplary embodiments, the stripping buffer that is utilized in the methods described herein comprises buffered, arginine, urea and dithiothreitol (DTT). The methods described herein can also utilize 3-, 4-, 5-, 6-, 7-, 8-, 9-, 10-, etc, column cycles, as desired, with stripping with the described stripping buffer between each consecutive cycle.

It has been surprisingly found that the use of a stripping buffer between consecutive cycles having the composition described herein, suitably comprising urea and arginine, results in an increased yield of the final immunoconjugate, as compared to elution methods and columns that do not utilize a stripping buffer as described herein between consecutive elutions.

In embodiments, the yield of recovered immunoconjugate is suitably at least about 20% greater, at least about 30% greater, at least about 40% greater, at least about 50% greater, at least about 60% greater, at least about 70% greater, at least about 80% greater, at least about 90% greater, at least about 100% greater, at least about 125% greater, at least about 150% greater, at least about 175% greater, at least about 200% greater, at least about 300% greater, at least about 400% greater, at least about 500% greater, at least about 600% greater, at least about 700% greater, at least about 800% greater, at least about 900% greater, etc., in comparison to elution methods and columns that do not utilize a stripping buffer as described herein between consecutive elutions In suitable embodiments, the stripping buffer useful in the methods described herein comprises about 0.10 to about 0.9 M arginine, about 5-10 M urea and about 7-15 mM DTT. More suitably, the stripping buffer comprises, about 0.25 to about 0.75 M arginine, about 7-9 M urea and about 9-11 mM DTT. More suitably, about 0.45 to about 0.55 M arginine, about 7.5-8.5 M urea and about 9.5-10.5 mM DTT. Most suitably, the stripping buffer comprises about 0.50 M arginine, about 8.0 M urea and about 10.0 mM DTT.

In the various methods described herein, the refolding buffer that is utilized in the refolding steps described herein has a pH of less than or about 10.0, suitably less than or about 9.5, and more suitably less than or about 9.4 (e.g., a pH of about 10.0, about 9.9, about 9.8, about 9.7, about 9.6, about 9.5, about 9.3, about 9.2, about 9.1 or about 9.0). It has been surprisingly found that the use of a refolding buffer having a pH of less than or about 10.0, less than or about 9.5 and most suitably less than about 9.4, results in an increased yield of the final immunoconjugate, as compared to processes that utilize refold buffers having pHs greater than these recited values.

In embodiments, the yield of recovered immunoconjugate is suitably at least about 20% greater, at least about 30% greater, at least about 40% greater, at least about 50% greater, at least about 60% greater, at least about 70% greater, at least about 80% greater, at least about 90% greater, at least about 100% greater, at least about 125% greater, at least about 150% greater, at least about 175% greater, at least about 200% greater, at least about 300% greater, at least about 400% greater, at least about 500% greater, at least about 600% greater, at least about 700% greater, at least about 800% greater, at least about 900% greater, etc., in comparison to processes that utilize refold buffers having pHs greater than these recited values.

In the various preparation methods described herein, suitably the immunoconjugate comprises an antibody or antigen binding fragment thereof. As described throughout, suitably the antibody or antigen binding fragment comprises a Fab, a Fab', a F(ab')2, a Fd, a single chain Fv or scFv, a disulfide linked Fv, a V-NAR domain, an IgNar, an intrabody, an IgGΔCH2, a minibody, a F(ab')$_3$ a tetrabody, a triabody, a diabody, a single-domain antibody, DVD-Ig, Fcab, mAb$_2$, a (scFv)$_2$, or a scFv-Fc.

As described herein, suitably the antibody or antigen binding fragment of the immunoconjugate binds a cell surface receptor. An exemplary cell surface receptor includes CD22.

In suitable embodiments, the immunoconjugate that is prepared according to the methods described herein comprises a toxin. Exemplary toxins and methods of preparing such toxins are described throughout. Suitably, the toxin is selected from the group consisting of: *Pseudomonas* exotoxin, ricin, abrin, diphtheria toxin and subunits thereof, as well as botulinum toxins A through F or variants, or derivatives thereof. In embodiments, the toxin is a *Pseudomonas* exotoxin, or variant thereof. Exemplary methods of preparing *Pseudomonas* exotoxin (PE) are described herein in detail as well as in WO2012/015912.

In embodiments, the *Pseudomonas* exotoxin for use in the immunoconjugates described herein has an amino acid sequence selected from the group consisting of SEQ ID NOs: 16-22. Suitably, the *Pseudomonas* exotoxin, or variant thereof has the amino acid sequence of SEQ ID NO:22.

Suitably, the antibody or antigen binding fragment thereof that is a component of the immunotoxin comprises a VH and a VL sequence. Suitably, the VH sequence is selected from the group consisting of SEQ ID NOs: 6-11, and the VL sequence is selected from the group consisting of SEQ ID NOs: 2, and 12-15.

As described throughout, the methods of preparing immunoconjugates are suitably used for preparing immunoconjugates that comprise an anti-CD22 antibody or antigen binding fragment thereof and a PE or variant thereof. In suitable embodiments the immunoconjugate that is prepared by the various methods described herein is the Moxetumomab pasudotox immunotoxin comprising the VH-PE38 subunit of SEQ ID NO: 1 and the VL subunit of SEQ ID NO:2.

In further embodiments, methods of preparing an active immunoconjugate are provided that combine the various processes described herein that have been determined to increase the yield of an active immunoconjugate. Suitably, the immunoconjugate is deamidated at one or more residues, and the deamidation results in an inhibition of potency of the immunoconjugate.

As described herein, such methods suitably comprise refolding an immunoconjugate with a fed-batch process in a refold buffer having a pH of less than 9.5 and purifying the refolded immunoconjugate with a two cycle elution on an ion exchange column, wherein the column is stripped between a first elution and a second elution with a stripping buffer comprising ethanolamine, arginine, Ethylenediaminetetraacetic acid (EDTA), urea and dithiothreitol (DTT).

Suitably, the various methods described herein provide an amount of the immunoconjugate recovered from the methods that is at least three-hundred % (300%) greater than an amount of the immunoconjugate recovered utilizing a method that does not comprise a fed-batch refolding process and/or a two cycle elution on an ion exchange column that has been stripped using the described stripping buffer and/or does not utilize a refolding buffer having a pH less than 9.4.

In embodiments, the amount of recovered immunoconjugate is suitably at least about 20% greater, at least about 30% greater, at least about 40% greater, at least about 50% greater, at least about 60% greater, at least about 70% greater, at least about 80% greater, at least about 90% greater, at least about 100% greater, at least about 125% greater, at least about 150% greater, at least about 175% greater, at least about 200% greater, at least about 300% greater, at least about 400% greater, at least about 500% greater, at least about 600% greater, at least about 700% greater, at least about 800% greater, at least about 900% greater, etc., in comparison to processes that does not comprise a fed-batch refolding process and/or a two cycle elution on an ion exchange column that has been stripped using the described stripping buffer and/or does not utilize a refolding buffer having a pH less than 9.4.

As described herein, suitably the immunoconjugate comprises an antibody or antigen binding fragment thereof, including an antibody or antigen binding fragment of the immunoconjugate binds a cell surface receptor such as CD22.

In suitable embodiments, the immunoconjugate comprises a toxin, suitably *Pseudomonas* exotoxin (PE). Suitably, the antibody or antigen binding fragment thereof that is a component of the immunotoxin comprises a VH and a VL sequence. Suitably, the VH sequence is selected from the group consisting of SEQ ID NOs: 6-11, and the VL sequence is selected from the group consisting of SEQ ID NOs: 2, and 12-15. As described throughout, the methods of preparing immunoconjugates are suitably used for preparing immunoconjugates that comprise an anti-CD22 antibody or antigen binding fragment thereof and a PE or variant thereof. In suitable embodiments the immunoconjugate that is prepared by the various methods described herein is the Moxetumomab pasudotox immunotoxin comprising the VH-PE38 subunit of SEQ ID NO: 1 and the VL subunit of SEQ ID NO:2.

In additional embodiments, compositions comprising an immunoconjugate prepared by the various methods described herein are provided. Suitably, the immunoconjugates prepared by such methods have less than between about 25% and about 1% deamidated species. More suitably, less than about 25% of the deamidated species is present, or less than about 20% of the deamidated species is present, or less than about 10% of the deamidated species is present, or less than about 5% of the deamidated species is present, or less than about 3% of the deamidated species is present, or less than about 2% of the deamidated species is present, or less than about 1% of the deamidated species is present.

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

EXAMPLES

Example 1: Renaturation and Purification of Moxetumomab Pasudotox

Introduction

CAT-8015 (Moxetumomab pasudotox) is a recombinant immunotoxin produced in *E. coli* inclusion bodies. Generation of active Moxetumomab pasudotox suitably utilizes refolding from inactive pre-cursors and purification of the refolded product by a 4-column process. FIG. 1 provides an overview of the renaturation and purification processes.

The purpose of the solubilization process is to extract and transfer VH and VL suitably from insoluble inclusion bodies into the liquid phase and to denature both subunits prior to refolding. Depth filtration removes insoluble cell debris and inclusion body components from solubilized VH and VL. The filtrate is subsequently concentrated by tangential flow filtration to a fixed retentate weight, which is determined by the retentate dilution factor and final refold weight. The function of the concentration step is to ensure consistent refold starting conditions in terms of VH and VL concentrations and Dithiothreitol (DTT) to oxidized glutathione ratio.

The objective of the 4 column purification process is to separate correctly-folded, active Moxetumomab pasudotox from product-related contaminants, such as misfolded product variants, aggregates, fragments and biologically inactive product charge isoforms as well as process-related contaminants including host cell DNA, host cell proteins and endotoxins.

In order to achieve a commercially viable process, refold and purification yields are maximized while maintaining product quality, activity and safety. The methods and procedures described herein have been developed for the manufacture of immunoconjugates, including the Moxetumomab pasudotox drug substance.

A. Materials and Methods

1. Inclusion Body Solubilization

VH-PE38 (VH) and VL inclusion bodies produced from suitable cells are thawed for 12-24 hours at room temperature. The VH and VL IB solubilization starting concentration are 0.3 g VH per liter refold and 0.07 g VL per liter refold. Inclusion bodies are combined in a 1:1 molar ratio of VH to VL and adjusted to a final VH concentration of 10 g/L by adding Tris/EDTA buffer (50 mM Tris, 20 mM EDTA, pH 7.4). Inclusion bodies are solubilized by adding 6 kg inclusion body solubilization buffer (50 mM ethanolamine, 8M urea, 0.5 M arginine, 2 mM EDTA, 10 mM DTT, pH 9.3±0.1) to each kg of concentration-adjusted inclusion body solution. Solubilization is carried out for 90±15 minutes at room temperature with constant stirring.

2. Inclusion Body Clarification and Ultrafiltration 1

Solubilized inclusion bodies are clarified by filtration through a series of depth filters (see WO 2012/059212). The clarified filtrate is concentrated by tangential flow filtration to ⅒th of the final refold weight using a 5 kDa molecular weight cutoff (MWCO) ultrafiltration membrane.

3. Refolding and Ultrafiltration/Diafiltration 2

Moxetumomab pasudotox is refolded by a 10-fold (w/w) dilution of the clarified and concentrated inclusion body filtrate into pre-chilled (2-8° C.) refolding buffer (50 mM ethanolamine, 1 M arginine, 2 mM EDTA, 1.0 mM oxidized glutathione, pH 9.4). The addition (L/hr) is set so that the clarified and concentrated inclusion body filtrate is added to pre-chilled refold buffer over the course of 4 hours (suitably 26 mL solubilized inclusion bodies per L refold buffer per hour). The refold reaction is allowed to proceed for 48-72 hours at 2-8° C. with continuous mixing and is warmed to room temperature prior to concentration and diafiltration.

The refold solution is concentrated by tangential flow filtration with a 10 kDa MWCO membrane and then diafiltered with 10 volumes of TMAE equilibration buffer (20 mM phosphate, pH 7.4).

4. Column Chromatography a. Fractogel TMAE (M) Chromatography

The concentrated and diafiltered refold solution is sterile filtered through a 0.2 μm filter and loaded onto a Fractogel TMAE column (EMD Biosciences or equivalent) equilibrated with 10 column volumes (CVs) TMAE equilibration buffer (20 mM phosphate buffer, pH 7.4). The chromatography steps are performed at a linear flow rate of 200 cm/hr unless otherwise noted. After loading, the column is first washed with 4 CVs TMAE equilibration buffer (20 mM phosphate, pH 7.4), followed by a 6 CV wash with wash buffer 1 (20 mM phosphate, 0.1% Triton X-100) and a 4 CV wash with wash buffer 2 (20 mM phosphate, 100 mM NaCl, pH 7.4). The product is eluted from the column with 3 CVs elution buffer (20 mM phosphate, 200 mM sodium chloride pH 7.4. After elution the column is stripped with 3 CVs stripping buffer (50 mM ethanolamine, 0.5 M arginine, 2 mM EDTA, 8 M urea, 10 mM DTT, pH 9.3). The flow rate may be reduced during the strip step. The column is subsequently washed with 3 CVs water for injection (WFI) and regenerated with 3 CVs regeneration solution (2M NaCl). The column is sanitized with at least 3 CVs sanitization solution (1 N sodium hydroxide) and stored with 3 CVs short term storage solution (0.1 N sodium hydroxide) or 3 CVs long term storage solution (20 mM phosphate, 20% (w/v) ethanol, pH 7.4).

b. Hydroxyapatite Chromatography

The hydroxyapatite chromatography step is operated as a flow-through chromatography step. The chromatography steps are performed at a linear flow rate of 250 cm/hr unless otherwise noted. The capture step product is loaded onto a ceramic hydroxyapatite column (Bio-Rad Laboratories or equivalent) equilibrated with 5 CVs pre-equilibration buffer (400 mM phosphate, 200 mM sodium chloride, pH 7.4) and 5 CVs equilibration buffer (20 mM potassium phosphate, 200 mM sodium chloride, pH 7.4). The product is collected in the flow-through fraction. After loading, the column is washed with 3 CVs equilibration buffer. The column is regenerated with 3 CVs pre-equilibration buffer, sanitized with 3 CVs sanitization buffer (1 N sodium hydroxide) and stored in 3 CVs storage buffer (10 mM phosphate, 0.1 N sodium hydroxide) at room temperature.

c. Phenyl 650 M Chromatography and Ultrafiltration/Diafiltration 3

The hydroxyapatite product is diluted at a 1:1 ratio (w/w) with load preparation buffer (20 mM phosphate, 1.2 M sodium sulfate, pH 7.4) and loaded onto a Phenyl 650 M column (Tosoh or equivalent) equilibrated with 5 CVs equilibration buffer (20 mM phosphate, 0.6 M sodium sulfate, pH 7.4). After loading, the column is washed with 1 CV equilibration buffer. The product is eluted with a 20 CV linear gradient from 0 to 100% elution buffer (20 mM sodium phosphate, pH 7.4). The column is stripped with 2 CVs water for injection and regenerated with 2 CVs 8 M urea. The column is sanitized with 3 CVs sanitization buffer (0.5 N sodium hydroxide) and stored with 3 CVs storage buffer (20 mM phosphate, 20% (w/w) ethanol, pH 7.4) at room temperature.

The Phenyl 650 M product pool is diafiltered with 10 volumes of 10 mM Tris, pH 8.0, using tangential flow filtration with a 10 kDa MWCO membrane.

d. Q Sepharose HP Chromatography and Ultrafiltration/Diafiltration 4

The diafiltered Phenyl 650 M product is loaded onto a Q Sepharose HP column (GE Healthcare or equivalent), pre-equilibrated with 5 CVs pre-equilibration buffer (10 mM Tris, 1 M sodium chloride, pH 8.0, and equilibrated with 5 CVs equilibration buffer (10 mM Tris, pH 8.0). The column is washed with 1 CV equilibration buffer and then washed with 3CVs 65% (v/v) equilibration buffer, 35% (v/v) elution buffer (10 mM Tris, 0.5 M sodium chloride, pH 8.0). The product is eluted with a 10 CV linear gradient from 65% (v/v) equilibration buffer, 35% (v/v) elution buffer to 45% (v/v) equilibration buffer, 55% (v/v) elution buffer. The column is stripped with 2 CVs pre-equilibration buffer and sanitized with 3 CVs sanitization buffer (1 N sodium hydroxide). The column is stored either in 3 CVs short term storage solution (0.1 N sodium hydroxide) or 3 CVs long term storage solution (20 mM phosphate, 20% (w/v) ethanol, pH 7.4).

The Q Sepharose HP product is concentrated by tangential flow filtration using a 10 kDa MWCO membrane to a target protein concentration of 1.3-2 mg/mL. The concentrated Q Sepharose product is diafiltered with at least six volumes of formulation buffer (25 mM sodium phosphate, 4% (w/v) sucrose, 8% (w/v) glycine, pH, 7.40). The diafiltered Q Sepharose HP product is diluted with formulation buffer to a final protein concentration of 0.95-1.05 mg/mL.

5. Formation of Moxetumomab Pasudotox Drug Substance (DS)

The diafiltered Q Sepharose HP product is diluted with formulation buffer to a final protein concentration of 0.95-1.05 mg/mL and subsequently adjusted to 0.02% (w/v) polysorbate-80 with formulation spike solution (10% (w/v) polysorbate-80) to make the drug substance. The drug substance is 0.2 μm filtered into sterile HDPE bottles and stored at ≤−70° C.

Example 2: Moxetumomab Pasudotox 250 Liter Refold, Trial 1

A. Materials and Methods

1. Filters and Membranes

C0HC and X0HC Millistak+HC POD filters (0.55 m$^2$ each) were from Millipore. Pellicon 2 BioMax-5 (V screen, 2 m$^2$) and Pellicon 2 BioMax-10 (A screen, 0.5 and 2.5 m$^2$) tangential flow filtration membranes were from Millipore. Durapore Millipak 20, SHC Opticap XL150 and SHC Opticap XL300 filters were from Millipore.

2. Chromatography Media and Instrumentation

Fractogel TMAE (M) was from EMD. Hydroxyapatite, Type 1, 40 μm, was from BioRad. Phenyl 650 M was from Tosoh. Q Sepharose HP was from GE Healthcare. Fractogel TMAE purification was performed in a BPG 140×500 column (GE Healthcare). Hydroxyapatite and Phenyl 650 M purification was performed in a BPG 100×500 column. Q Sepharose HP purification was performed in a Millipore QuikScale 70×550 column (Millipore). All purifications were performed on an AKTA Pilot chromatography system.

3. Renauration at the 250 Liter Refold Scale 3.39 kg VH inclusion body (IB) slurry and 0.33 kg VL IB slurry were diluted with 3.77 kg TE buffer to a final VH concentration of 10 g/L. IBs were solubilized with 44.9 kg of IB solubilization buffer for 90 minutes at room temperature. The solubilized IB solution was clarified with a C0HC depth filter (0.55 m²) connected in series with a X0HC depth filter (0.55 m²). The solubilized and clarified IB solution was concentrated to a final ultrafiltrate (UF) 1 retentate weight of 25.5 kg by tangential flow filtration using a Pellicon 2 BioMax-5 (V screen, 2 m²) membrane. Twenty five kg of UF 1 retentate were temperature adjusted to 2-8° C. and added in the course of 4 hours to 225 kg pre-chilled refold buffer (pH 9.4) with constant mixing (suitably 26 mL solubilized inclusion bodies per L refold buffer per hour). The refold was terminated after 66 hours by increasing the temperature of the refold solution to room temperature. The refold solution was concentrated to 24.9 kg by tangential flow filtration using a Pellicon 2 BioMax-10 (A screen, 2.5 m2) membrane and subsequently diafiltered with 10 volumes TMAE equilibration buffer.

4. Purification at the 200 Liter Refold Scale

Purification of Moxetumomab pasudotox was executed as described above. 9.9 L and 9.3 L of concentrated and diafiltered refold solution were loaded onto a packed Fractogel TMAE (M) column (bed height: 18 cm, volume: 2.77 L). Two purification cycles were performed (with stripping buffer utilized between consecutive elutions). The Fractogel TMAE (M) eluate fractions were combined into a single TMAE product pool (7.1 kg) and loaded onto a hydroxyapatite column (bed height: 21.8 cm; volume: 1.71 L). The hydroxyapatite flow through pool was diluted 1:1 with 7.91 kg load preparation buffer and loaded onto a Phenyl 650M column (bed height: 17.5 cm; volume: 1.37 L). The Phenyl 650M product pool (11.6 kg) was concentrated to 8.1 kg by tangential flow filtration with using a Pellicon 2 BioMax-10 membrane (A screen, 0.5 m²) and subsequently diafiltered with 10 volumes Q Sepharose HP equilibration buffer. The concentrated and diafiltered Phenyl 650 M product was loaded onto a Q Sepharose HP column (Bed height: 18.2 cm; volume 0.70 L). The Q Sepharose HP product pool (2.8 kg) was concentrated to 2 g/L by tangential flow filtration using a Pellicon 2 BioMax-10 (A screen, 0.5 m²) membrane and subsequently diafiltered with 7 volumes formulation buffer. The concentrated and diafiltered Q Sepharose HP product was diluted with formulation buffer to a final protein concentration of 1.02 g/L (volume: 4.7 kg) and subsequently adjusted to 0.02% (w/v) polysorbate-80 with formulation spike solution. Formulated Moxetumomab pasudotox was sterile filtered with Durapore Millipak 20 filters into PETG bottles and stored at ≤−70° C.

B. Results and Discussion

1. Renaturation

Solubilization, clarification and UF 1 step yields were evaluated by RP-HPLC and are shown in Tables I and II. Clarification efficiency was evaluated by turbidity measurements before and after depth filtration (Table III).

TABLE I $V_H$ Recovery (%) for Pre-Refold Unit Operations

| Step | Volume (kg) | Concentration (g/L) | Total $V_H$ (g) | Step Yield (%) |
| --- | --- | --- | --- | --- |
| IB Slurry | 3.4 | 22.1 | 75.0 | NA |
| Solubilization | 52.4 | 2.0 | 104.8 | 140.0 |
| Clarification | 55.1 | 1.7 | 93.7 | 89.4 |
| UF 1 | 25.5 | 3.2 | 81.6 | 87.1 |
| Overall Yield | | | | 109.0 |

TABLE II $V_L$ Recovery (%) for Pre-Refold Unit Operations

| Step | Volume (kg) | Concentration (g/L) | Total $V_L$ (g) | Step Yield (%) |
| --- | --- | --- | --- | --- |
| IB Slurry | 0.3 | 52.4 | 15.7 | NA |
| Solubilization | 52.4 | 0.4 | 21.0 | 133.7 |
| Clarification | 55.1 | 0.3 | 16.5 | 78.8 |
| UF 1 | 25.5 | 0.6 | 15.3 | 92.6 |
| Overall Yield | | | | 97.6 |

TABLE III

Clarification Efficiency of Depth Filtration Unit Operation

| Step | Turbidity (NTU) |
| --- | --- |
| Solubilized IB solution (before filtration) | 32 |
| Clarified IB solution (after filtration) | 4.3 |

The data in Tables IV and II demonstrates the effectiveness of the IB solubilization buffer composition in extracting and transferring VH and VL from inclusion bodies into the liquid phase. Both subunits were quantitatively recovered in the solubilized IB solution. The C0HC-X0HC depth filter train achieved an 8-fold reduction in turbidity of the solubilized IB solution and produced an optically clear solution suitable for further processing by tangential flow filtration. Clarification step yields were comparable for VH and VL (89.4 and 78.8% respectively) despite the 4-fold difference in molecular weight of the two subunits. The optimal performance of the pre-refold unit operations is demonstrated by the fact that the final UF 1 VH yield met the required amount to achieve a target refold concentration of 0.3 g VH per L refold.

Refolding of Moxetumomab pasudotox was initiated by 10-fold dilution of UF 1 retentate into refold buffer. The UF 1 retentate was added over the course of 4 hours to the refold buffer to maximize refold yields. The Moxetumomab pasudotox refold titer was determined by LC-MS, the Moxetumomab pasudotox concentration in the UFDF 2 pool by RP-HPLC. Refold yield was calculated based on the initial VH concentration in the refold reaction, based on dilution ratio and the RP-HPLC concentration of VH in the UF 1 retentate pool. Refold titer, Moxetumomab pasudotox UFDF2 concentration and step yields are shown in Table IV.

TABLE IV

Refold and UFDF Step Yields

| Step | Volume (kg) | Moxetumomab pasudotox Conc. (g/L) | Total Moxetumomab pasudotox (g) | Step Yield (%) |
| --- | --- | --- | --- | --- |
| Refold Product | 250 | 0.068 | 17.1 | 17.3 |
| UFDF2 Product | 25 | 0.59 | 14.8 | 86.9 |

Refolding of heterodimeric proteins represents a significant challenge due to the fact that the separate subunits can proceed along multiple unproductive folding pathways and form insoluble aggregates or misfolded inactive product variants. Refolding of heterodimeric proteins is therefore often characterized by low refold titers and step yields. Refold conditions described herein have been carefully optimized toward efficient utilization of inclusion bodies starting material and maximizing refold titers (Table IV). As a result, refold titers and step yields were approximately 2-3 fold higher compared to previous refold processes.

The function of the post-refold tangential flow filtration unit operation is to terminate the refold by removing refold buffer components and preparing the refolded material for capture step purification. A step yield of nearly 87% refolded Moxetumomab pasudotox was within the expected range for this type of unit operation and starting material.

The data in Tables III-IV demonstrates the performance of the disclosed methods and the capability of this process to generate biologically active Moxetumomab pasudotox from inactive pre-cursors suitable for manufacturing of Moxetumomab pasudotox drug substance.

2. Purification

Moxetumomab pasudotox was purified from concentrated and diafiltered refold solution at the 200 L refold scale by Fractogel TMAE (M), Hydroxyapatite, Phenyl 650 M and Q Sepharose HP chromatography. Chromatograms for each purification step are shown in FIGS. 2-5.

The Fractogel TMAE (M) chromatogram shows that not only refolded Moxetumomab pasudotox, but also most the product- and process-related impurities bound to the column with little or no protein detected in the column flow through fraction. Some hydrophobically-bound impurities were removed from the column with the non-ionic detergent Triton X-100 (wash 1) whereas weak ionically-bound impurities were removed with a low concentration salt wash (wash 2). Elution of folded Moxetumomab pasudotox was achieved with buffered 200 mM sodium chloride. Most of the bound impurities were stripped from the Fractogel TMAE column with IB solubilization buffer (strip 1). The effectiveness of this buffer for column cleaning purposes is demonstrated by the observation that very little protein was eluted off the column during a second strip with 2M sodium chloride (strip 2).

Figure 3:
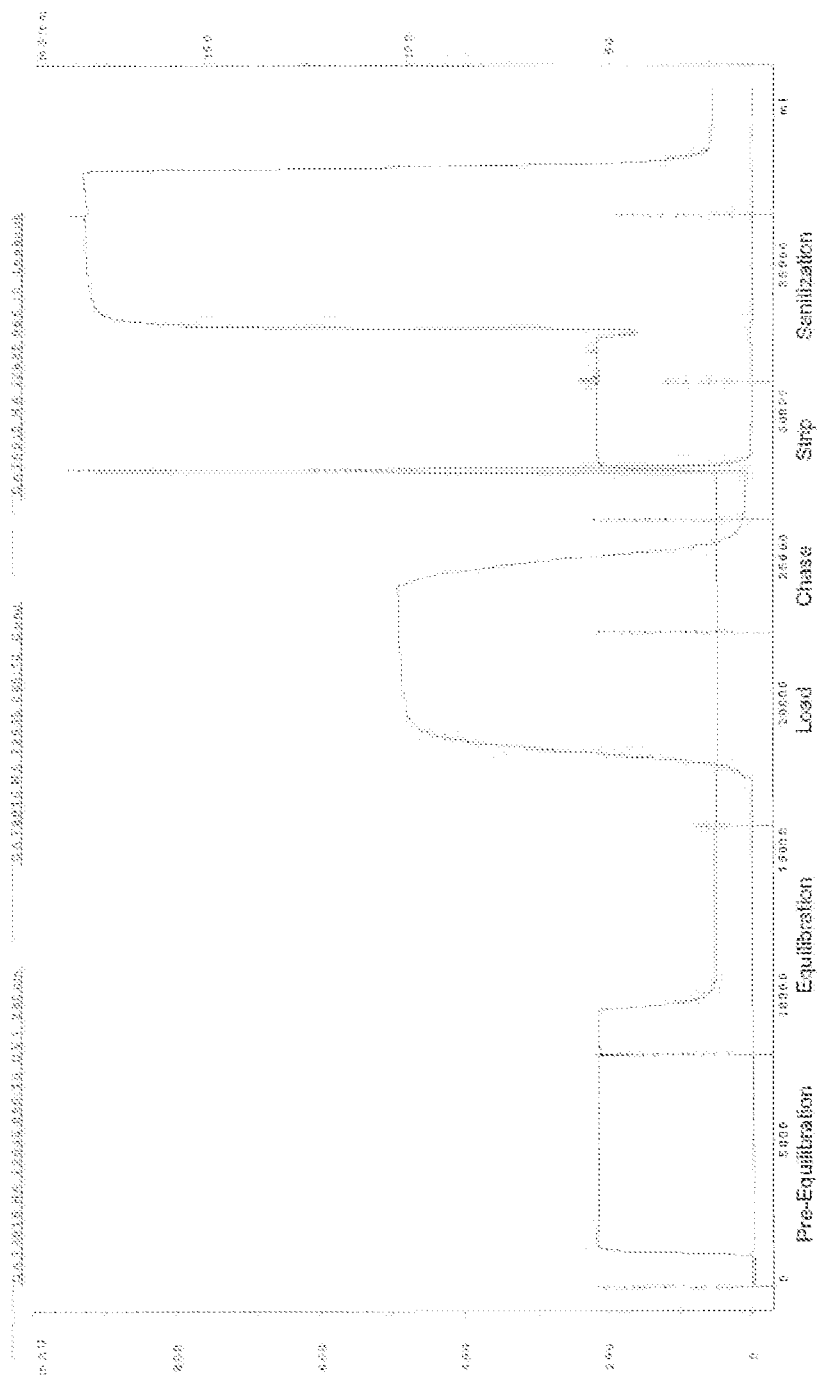
FIG. 3 shows the results of a hydroxyapatite chromatography.
Figure 4:
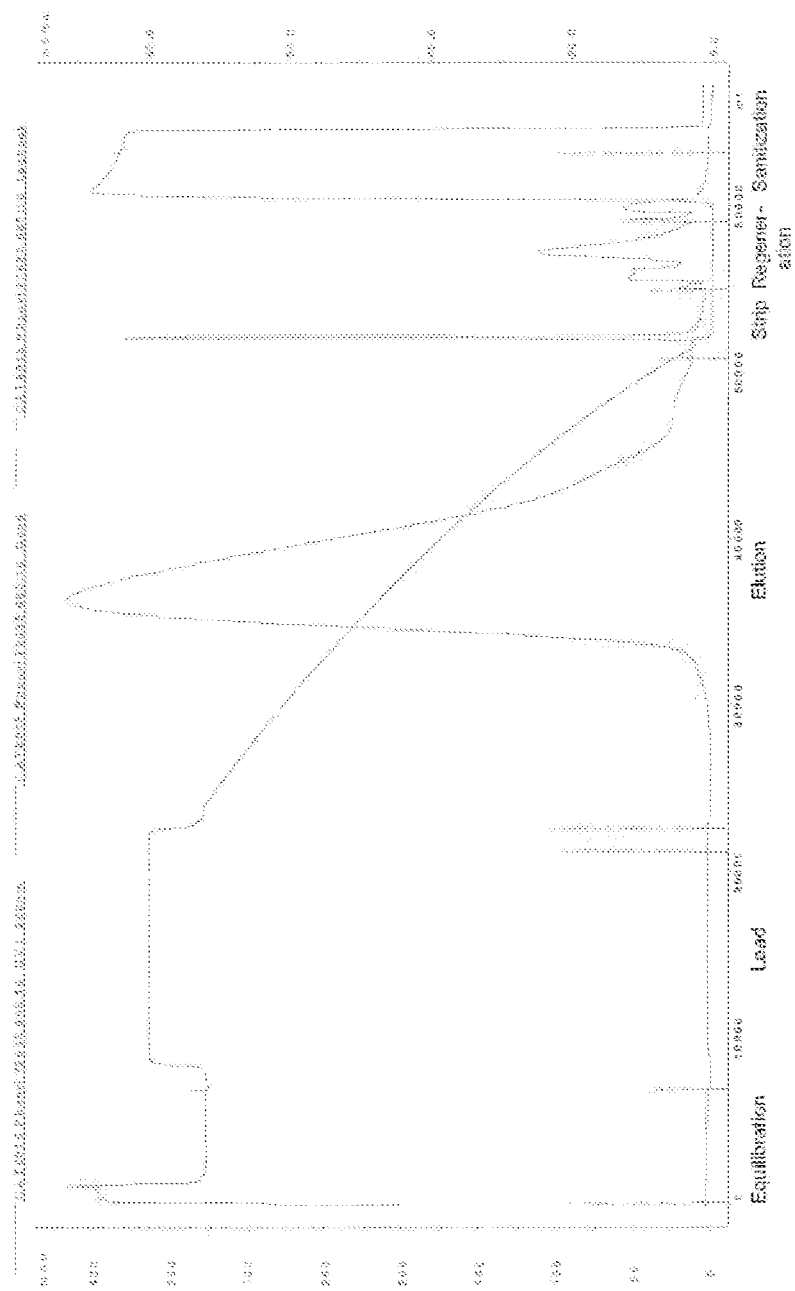
FIG. 4 shows the results of a Phenyl 650 M chromatography.

The chromatogram in FIG. 3 shows that Moxetumomab pasudotox did not bind to hydroxyapatite in the presence of 20 mM phosphate and was recovered in the flow through fraction. Process-related contaminants such as host cell proteins, DNA and endotoxin bound tightly to hydroxyapatite under these conditions and were subsequently removed from the resin with a 400 mM phosphate, 200 mM sodium chloride strip buffer.

The chromatogram shows that Moxetumomab pasudotox and product- and process-related impurities bound to Phenyl 650 M resin with little or no protein detected in the column flow through fraction. Moxetumomab pasudotox was eluted with a decreasing salt gradient and recovered from the column in the conductivity range 60-30 mS/cm. Product and process related impurities were stripped from the column with a water wash (Strip) and 8M urea solution (Regeneration). The effectiveness of the post elution cleaning protocol is demonstrated by the observation that an increase in absorbance at 280 nm is not seen during the 0.5N sodium hydroxide sanitization step.

Figure 5:
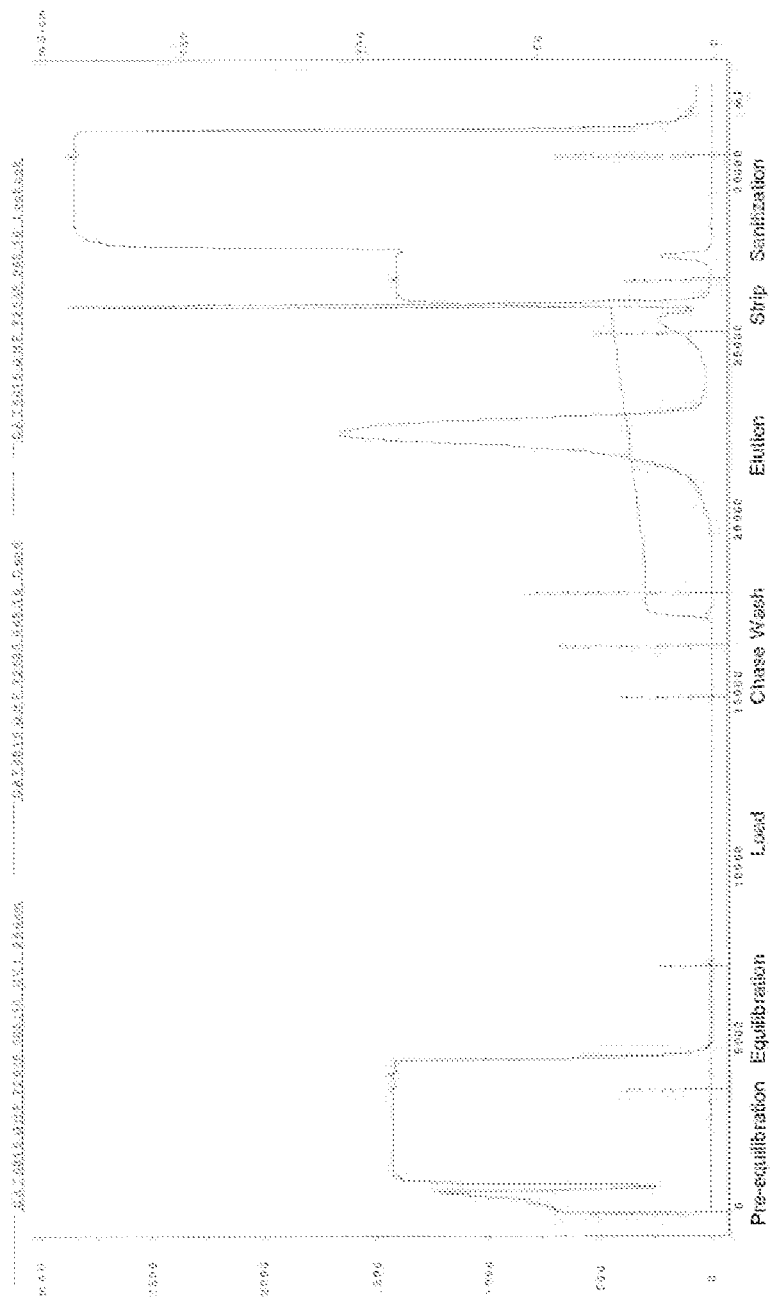
FIG. 5 shows the results of a Q Sepharose HP chromatography. Column load challenge was 10.4 g/L.

The Q Sepharose HP chromatogram in FIG. 5 shows that under the current binding conditions Moxetumomab pasudotox and product- and process-related impurities bound to the column No protein was detected in the column flow through fraction (Load, Chase) or wash fraction (Wash). Moxetumomab pasudotox was recovered from the column with an increasing, buffered salt gradient from 175 mM sodium chloride to 275 mM sodium chloride at pH 8.0. Moxetumomab pasudotox eluted off the column in a very narrow conductivity range between 21 and 24 mS/cm.

Remaining impurities were eluted from the column with a 1M sodium chloride strip and 1 N sodium hydroxide solution.

Total protein step yields were determined by absorbance measurements at 280 nm Total protein step yields for purification lot 250 L3 are shown in V.

TABLE V

Total Protein Step Yield Table

| Step | Pool Volume (kg) | Total Protein Yield (g) | Step Yield (%) |
|---|---|---|---|
| TMAE | 7.1 | 10.8 | 13.5 |
| HA | 8.2 | 9.7 | 96.1 |
| Phenyl | 11.6 | 8.0 | 92.5 |
| UFDF3 | 8.1 | 7.6 | 98.4 |
| QHP | 2.8 | 5.0 | 68.8 |
| UFDF4 | 4.7 | 4.6 | 102.2 |

The concentrated and diafiltered refold solution (UFDF2 product, TMAE load sample) contains refolded Moxetumomab pasudotox but also other proteins including misfolded and aggregated product variants and host cell proteins. Protein concentration measurements based on absorbance at 280 nm are therefore not specific for correctly folded Moxetumomab pasudotox and as a consequence do not reflect the Moxetumomab pasudotox specific yield of the Fractogel TMAE (M) capture step. In contrast, the total protein and Moxetumomab pasudotox step yields for the hydroxyapatite purification step are much more closely aligned with each other due the increased purity of the Fractogel TMAE (M) product pool (hydroxyapatite load) in which most of the product- and process-related impurities have been removed. High recoveries were also obtained for the subsequent purification and buffer exchange steps. The final purification yield was 4.6 g of drug substance at the 200 L refold scale and purification scale.

Table VI shows the clearance of product-related contaminants including deamidated Moxetumomab pasudotox, aggregates and fragments.

TABLE VI

Clearance of Product-Related Contaminants in Purification Process

| Step | IEC Pre-Peak (%) | HPSEC Purity Mon [a], Agg [b], Others [c] (%) | Fragment by RP-HPLC (%) |
|---|---|---|---|
| UFDF2 | NA | 85.0, 0.0, 15.0 | Not submitted |
| TMAE | 3.6, 4.2 | 96.2, 2.2, 1.5 | Not submitted |
| HA | 3.6 | 96.4, 2.1, 1.6 | Not submitted |
| Phenyl | 3.4 | 99.0, 1.0, 0.0 | 1.2 |
| QHP | 1.8 | 99.0, 1.0, 00 | 1.2 |

Figure 6:
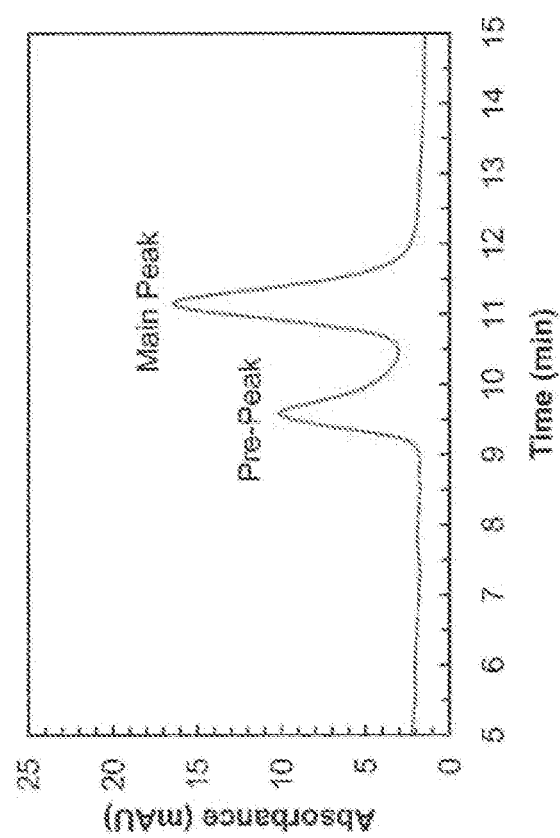
FIG. 6 shows the results of an IEC analysis of partially purified Moxetumomab pasudotox.
Figure 7:
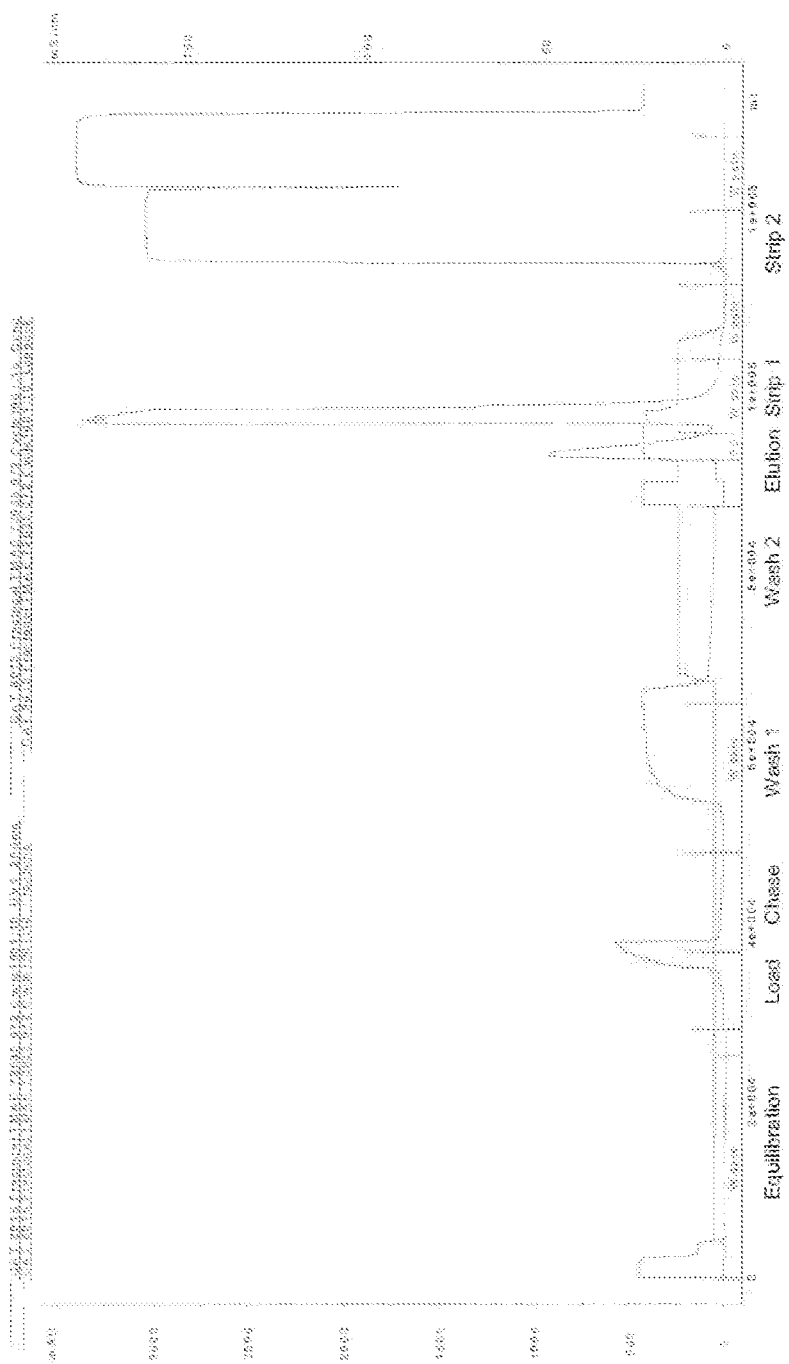
FIG. 7 shows the results of a Fractogel TMAE (M) capture Step (Cycle 1).

[a] Mon = Monomer
[b] Agg = Aggregates
[c] Others = fragments, low molecular weight proteins The biological activity of Moxetumomab pasudotox depends on the extent of deamidation of asparagine 358 in the VH subunit. Deamidation of Moxetumomab pasudotox was analyzed by high performance ion exchange chromatography (IEC) and correlates with the measured % pre-peak area (see FIG. 6).

The data in Table VI demonstrates that the IEC pre-peak area of Moxetumomab pasudotox in the TMAE product was less than 5% and that Q Sepharose HP chromatography reduced the IEC pre-peak area further to less than 2%, providing a biologically active product.

Fractogel TMAE (M) chromatography resulted in a significant increase in monomer purity and removed most of the low molecular weight proteins and fragments from the process stream as measured by high performance size exclusion chromatography (HPSEC). Phenyl 650 M chromatography provided additional clearance of fragments and aggregates and generated a Moxetumomab pasudotox product pool that had 99% monomer purity by HPSEC analysis.

Table VII shows the clearance of process-related contaminants including host cell proteins, DNA and endotoxins.

TABLE VII

Clearance of Process-Related Contaminants in Purification Process

| Step | HCP (ng/mg) | Endotoxin (EU/mg) | DNA (ng/mg) |
|---|---|---|---|
| UFDF2 | 1615 | 68134 | Not tested |
| Fractogel TMAE (M) | 312 | 109 | 0.88 |
| Hydroxyapatite | 40 | 3 | $<0.8 \times 10^{-3}$ |
| Phenyl 650 M | 6 | 2 | $<1.5 \times 10^{-3}$ |
| Q Sepharose HP | 2.8 | 0.1 | $<0.5 \times 10^{-3}$ |

Table VII illustrates the effectiveness of the Fractogel TMAE (M) capture step and hydroxyapatite chromatography in removing process-related contaminants from the Moxetumomab pasudotox process stream. Fractogel TMAE (M) chromatography reduced host cell protein concentrations over 5-fold and endotoxin concentrations over 600-fold. Hydroxyapatite chromatography further reduced host cell protein concentrations approximately 8-fold, endotoxin concentrations over 36-fold and residual DNA concentrations over a 1000-fold to below the limit of quantitation. Phenyl 650 M chromatography achieved an additional 6.5-fold reduction in host cell protein concentration whereas Q Sepharose HP chromatography provided an additional 20-fold reduction in endotoxin concentration.

The data in Tables VI and VII demonstrates the performance of the purification methods described herein and the capability of these processes to generate high quality drug substance suitable for clinical trials.

Example 3: Moxetumomab Pasudotox 250 Liter Refold, Trial 2

A. Materials and Methods

1. Filters and Membranes

C0HC and X0HC Millistak+HC POD filters (0.55 m2 each) were from Millipore. Pellicon 2 BioMax-5 (V screen, 2 m2) and Pellicon 2 BioMax-10 (A screen, 0.5 and 2.5 m2) tangential flow filtration membranes were from Millipore. Durapore Millipak 20, SHC Opticap XL150 and SHC Opticap XL300 filters were from Millipore.

2. Chromatography Media and Instrumentation

Fractogel TMAE (M) was from EMD. Hydroxyapatite, Type 1, 40 μm, was from BioRad. Phenyl 650 M was from Tosoh. Q Sepharose HP was from GE Healthcare. Fractogel TMAE purification was performed in a BPG 140×500 column (GE Healthcare). Hydroxyapatite, Phenyl 650 M and Q Sepharose HP purifications were performed in a BPG 100×500 column. All purifications were performed on an AKTA Pilot chromatography system.

3. Renaturation at the 250 Liter Refold Scale 3.40 kg VH IB slurry and 0.33 kg VL IB slurry were diluted with 3.77 kg TE buffer to a final VH concentration of 10 g/L. IBs were solubilized with 45.0 kg of IB solubilization buffer for 90 minutes at room temperature. The solubilized IB solution was clarified with a C0HC depth filter (0.55 m2) connected in series with a X0HC depth filter (0.55 m$^2$). The solubilized and clarified IB solution was concentrated to a final UF 1 retentate weight of 25.5 kg by tangential flow filtration using a Pellicon 2 BioMax-5 (V screen, 2 m$^2$) membrane. Twenty five kg of UF 1 retentate were temperature adjusted to 2-8° C. and added in the course of 4 hours to 225 kg pre-chilled refold buffer (pH 9.4) with constant mixing (suitably 25 mL solubilized inclusion bodies per L refold buffer per hour). The refold was terminated after 66 hours by increasing the temperature of the refold solution to room temperature. The refold solution was concentrated to 22.6 kg by tangential flow filtration using a Pellicon 2 BioMax-10 (A screen, 2.5 m2) membrane and subsequently diafiltered with 10 volumes TMAE equilibration buffer.

4. Purification at the 200 Liter Refold Scale

Purification of Moxetumomab pasudotox was executed as described above. Nine and 8.7 liters of concentrated and diafiltered refold solution were loaded onto a packed Fractogel TMAE (M) column (bed height: 18 cm, volume: 2.77 L). Two purification cycles were performed, stripping with the disclosed stripping buffer between consecutive elutions. The Fractogel TMAE (M) eluate fractions were combined into a single TMAE product pool (6.2 kg) and loaded onto a hydroxyapatite column (bed height: 21.8 cm; volume: 1.71 L). The hydroxyapatite flow through pool was diluted 1:1 with 6.7 kg load preparation buffer and loaded onto a Phenyl 650M column (bed height: 17.5 cm; volume: 1.37 L). The Phenyl 650M product pool (10.1 kg) was concentrated to 8.0 kg by tangential flow filtration with using a Pellicon 2 BioMax-10 membrane (A screen, 0.5 m$^2$) and subsequently diafiltered with 10 volumes Q Sepharose HP equilibration buffer. The concentrated and diafiltered Phenyl 650 M product was loaded onto a Q Sepharose HP column (Bed height: 18.2 cm; volume 1.4 L). The Q Sepharose HP product pool (5.1 kg) was concentrated to 2 g/L by tangential flow filtration using a Pellicon 2 BioMax-10 (A screen, 0.5 m$^2$) membrane and subsequently diafiltered with 7 volumes formulation buffer. The concentrated and diafiltered Q Sepharose HP product was diluted with formulation buffer to a final protein concentration of 1.05 g/L (volume: 5.4 kg) and subsequently adjusted to 0.02% (w/v) polysorbate-80 with formulation spike solution. Formulated Moxetumomab pasudotox was sterile filtered with Durapore Millipak 20 filters into PETG bottles and stored at ≤−70° C.

B. Results and Discussion

1. Renaturation

Solubilization, clarification and UF 1 step yields were evaluated by RP-HPLC and are shown in Tables VIII and IX. Clarification efficiency was evaluated by turbidity measurements before and after filtration (Table 3.2.2.1-3).

TABLE VIII $V_H$ Recovery (%) for Pre-Refold Unit Operations

| Step | Volume (kg) | Concentration (g/L) | Total $V_H$ (g) | Step Yield (%) |
|---|---|---|---|---|
| IB Slurry | 3.4 | 22.1 | 75.0 | NA |
| Solubilization | 52.5 | 2.1 | 110.3 | 147.7 |

TABLE VIII-continued

V<sub>H</sub> Recovery (%) for Pre-Refold Unit Operations

| Step | Volume (kg) | Concentration (g/L) | Total V$_H$ (g) | Step Yield (%) |
|---|---|---|---|---|
| Clarification | 57.8 | 1.9 | 109.8 | 99.6 |
| UF 1 | 25.5 | 4.6 | 117.3 | 106.8 |
| Overall Yield | | | | 157.1 |

TABLE IX

V$_L$ Recovery (%) for Pre-Refold Unit Operations

| Step | Volume (kg) | Concentration (g/L) | Total V$_L$ (g) | Step Yield (%) |
|---|---|---|---|---|
| IB Slurry | 0.3 | 52.4 | 15.7 | NA |
| Solubilization | 52.5 | 0.4 | 21.0 | 133.8 |
| Clarification | 57.8 | 0.3 | 17.3 | 82.6 |
| UF 1 | 25.5 | 0.8 | 20.4 | 117.6 |
| Overall Yield | | | | 129.2 |

TABLE X

Clarification Efficiency of Depth Filtration Unit Operation

| Step | Turbidity (NTU) |
|---|---|
| Solubilized IB solution (before filtration) | 35.7 |
| Clarified IB solution (after filtration) | 6.0 |

The data in tables VIII and IX shows that VH and VL were quantitatively recovered from the initial IB slurry in the UF 1 retentate pool as measured by RP-HPLC analysis. Depth filtration reduced the turbidity of the solubilized IB solution approximately 6-fold and produced an optical clear solution that was further concentrated by tangential flow filtration prior to refolding.

Refolding of Moxetumomab pasudotox was initiated by 10-fold dilution of UF 1 retentate into pre-chilled refold buffer over the course of 4 hours. The UF 1 retentate was kept at 2-8° C. during the addition to the refold buffer to minimize the generation of deamidated product variants. The Moxetumomab pasudotox refold titer was determined by LC-MS. The Moxetumomab pasudotox concentration in the UFDF 2 pool was determined by RP-HPLC. Refold step yield was calculated based on the initial VH concentration in the refold reaction, determined by the UF 1 VH concentration and dilution factor. Refold and UFDF2 step yields are shown in Table XI.

TABLE XI

Refold and UFDF Step Yields

| Step | Volume (kg) | Moxetumomab pasudotox Conc. (g/L) | Total Moxetumomab pasudotox (g) | Step Yield (%) |
|---|---|---|---|---|
| Refold Product | 250 | 0.058 | 14.1 | 10.2 |
| UFDF2 Product | 23 | 0.68 | 15.4 | 106.6 |

The refold titer was approximately 2 to 3-fold higher compared to previous Moxetumomab pasudotox refold processes. The step yield of 10% was comparable to previous Moxetumomab pasudotox refold processes.

The function of the post-refold tangential flow filtration unit operation is to terminate the refold by removing refold buffer components and preparing the refolded material for capture step purification. The step yield data in table XI shows that refolded Moxetumomab pasudotox was quantitatively recovered from the UFDF2 unit operation.

The data in tables VIII through IX demonstrates the performance of the disclosed methods and the capability of these processes to generate biologically active immunoconjugates (suitably Moxetumomab pasudotox) from inactive pre-cursors suitable for manufacturing of drug substance.

2. Purification

Moxetumomab pasudotox was purified from concentrated and diafiltered refold solution at the 200 L refold scale by Fractogel TMAE (M), Hydroxyapatite, Phenyl 650 M and Q Sepharose HP chromatography. Chromatograms for each purification step are shown in FIGS. 7-10.

The Fractogel TMAE (M) chromatogram shows that refolded Moxetumomab pasudotox and most the product- and process-related impurities bound to the column Breakthrough of protein was observed at the end of the load step; in contrast to purification in Example 2 in which protein break through at the end of the column load step was not detected.

Figure 8:
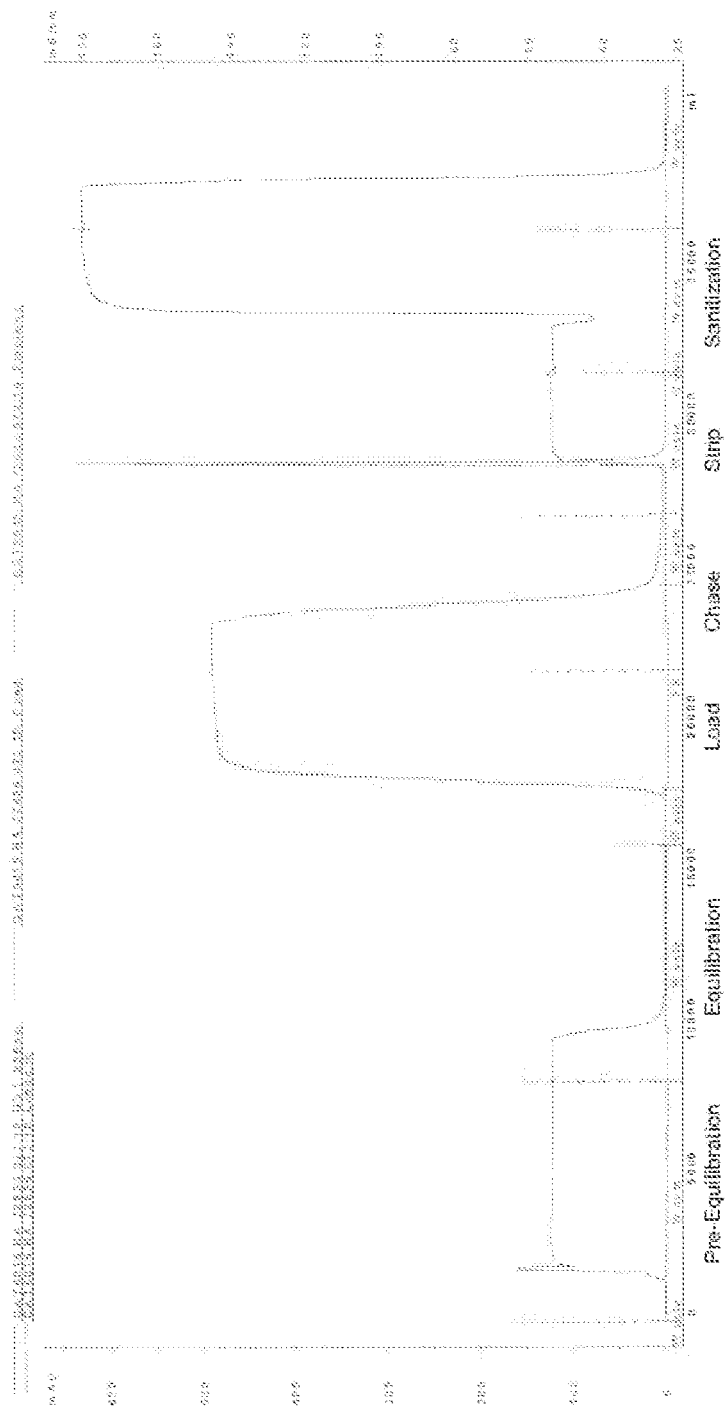
FIG. 8 shows the results of a Hydroxyapatite chromatography.

The chromatogram in FIG. 8 shows that Moxetumomab pasudotox did not bind to hydroxyapatite in the presence of 20 mM phosphate and was recovered in the flow through fraction.

Figure 9:
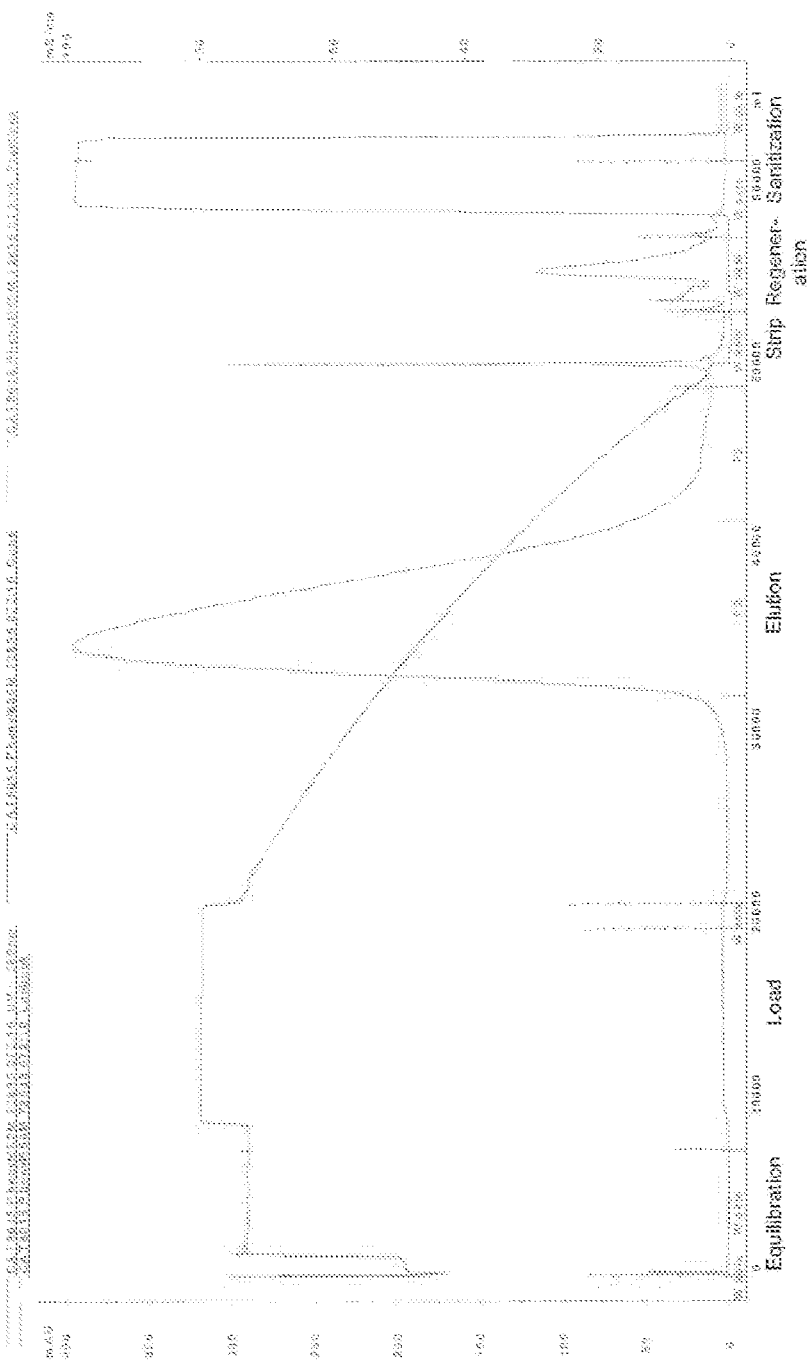
FIG. 9 shows the results of a Phenyl 650 M chromatography.

The chromatogram in FIG. 9 shows that Moxetumomab pasudotox and product- and process-related impurities bound to Phenyl 650 M resin with little or no protein detected in the column flow through fraction. Moxetumomab pasudotox was eluted with a decreasing salt gradient and recovered from the column in the conductivity range 60-30 mS/cm.

Figure 10:
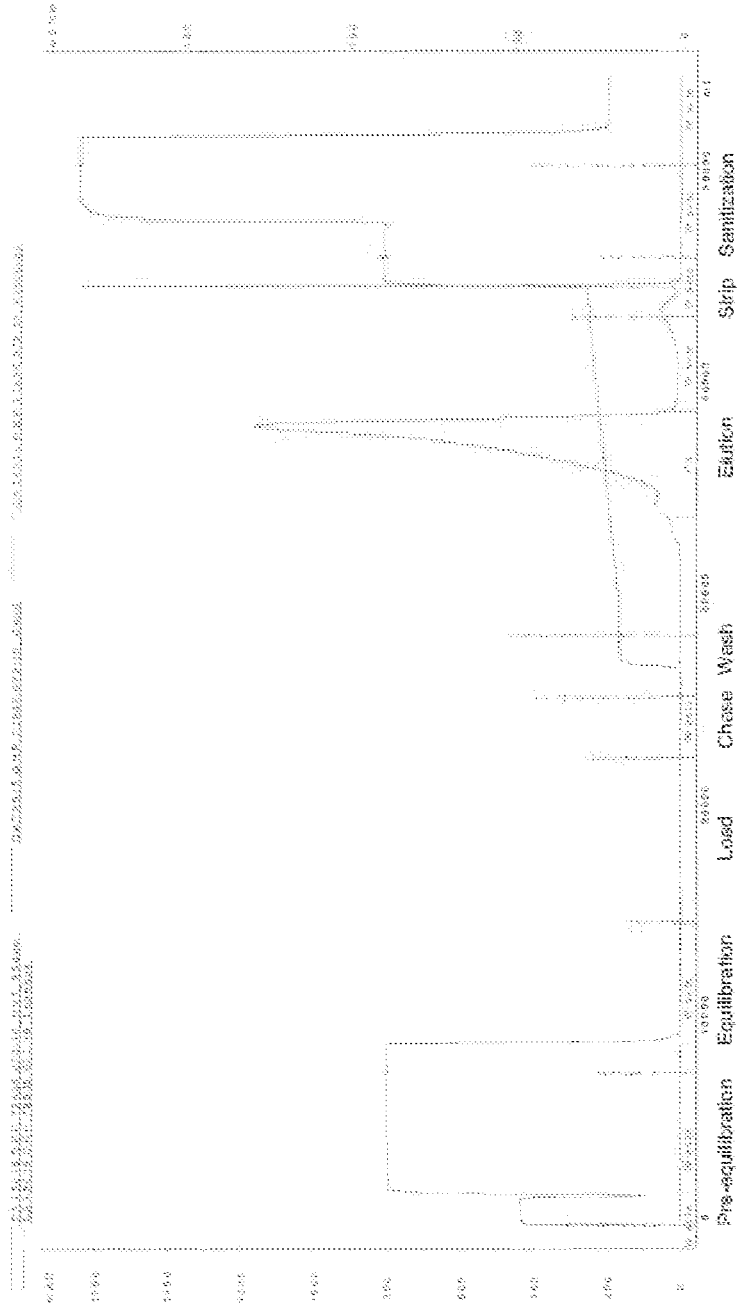
FIG. 10 shows the results of a Q Sepharose HP chromatography.

The Q Sepharose HP chromatogram in FIG. 10 shows Moxetumomab pasudotox and product- and process-related impurities bound to the column. No protein was detected in the column flow through fraction (Load, Chase) or wash fraction (Wash). Moxetumomab pasudotox was recovered from the column with an increasing, buffered salt gradient from 175 mM sodium chloride to 275 mM sodium chloride at pH 8.0. Active Moxetumomab pasudotox eluted off the column in a very narrow conductivity range between 21 and 24 mS/cm. Remaining impurities were eluted from the column with a 1M sodium chloride strip and 1 N sodium hydroxide solution.

Total protein step yields were determined by absorbance measurements at 280 nm Total protein step yields are shown in Table XII.

TABLE XII

Protein and Moxetumomab pasudotox Step Yield Table

| Step | Pool Volume (kg) | Total Protein Yield [a] (g) | Step Yield (%) |
|---|---|---|---|
| Fractogel TMAE (M) | 6.2 | 9.5 | 9.2 |
| Hydroxyapatite | 6.9 | 8.4 | 95.9 |
| Phenyl 650 M | 10.1 | 7.1 | 94.2 |
| UFDF3 | 8.0 | 6.3 | 92.0 |
| Q Sepharose HP | 5.1 | 5.5 | 88.4 |
| UFDF4 | 5.4 | 5.6 | 105.2 |

As above, the concentrated and diafiltered refold solution (UFDF2 product, TMAE load sample) contains refolded Moxetumomab pasudotox but also other proteins including misfolded and aggregated product variants and host cell proteins. Protein concentration measurements based on absorbance at 280 nm are therefore not specific for correctly folded Moxetumomab pasudotox and as a consequence does not reflect the Moxetumomab pasudotox specific yield of the Fractogel TMAE (M) capture step. In contrast, the total protein and Moxetumomab pasudotox step yields for the hydroxyapatite purification step are much more closely aligned with each other due the increased purity of the Fractogel TMAE (M) product pool (hydroxyapatite load) in which most of the product- and process-related impurities have been removed. The Phenyl 650 M and UFDF3 step yields for Example 3 were comparable to the step yields achieved in Example 2 for the same unit operations. Here the volume of the Q Sepharose HP column was increased from 0.7 L to 1.4 L to decrease the column load challenge for this purification step. As a result, the column load challenge decreased from 10.4 g/L resin in Example 2 to 4.5 g/L resin in Example 3. Q Sepharose HP step yield improved by nearly 20% from 69% in Example 2 to 88% in Example 3. Q Sepharose HP step yields were 2-3 fold higher compared to previous Moxetumomab pasudotox Q Sepharose HP process yields. The final purification yield was 5.6 g of drug substance at the 200 L refold scale and purification scale.

Table XIII shows the clearance of product related contaminants including deamidated Moxetumomab pasudotox, aggregates and fragments.

TABLE XIII

Clearance of Product Related Contaminants in Purification Process

| Step | IEC Pre-Peak (%) | HPSEC Purity Mon [a], Agg [b], Other [c] (%) | Fragments by RP-HPLC (%) |
|---|---|---|---|
| UFDF2 | NA | 87.2, 0.0, 12.8 | Not tested |
| TMAE | 7.8, 8.6 | 96.9, 1.6, 1.5 | Not tested |
| HA | 8.2 | 97.4, 1.5, 1.1 | Not tested |
| Phenyl | 5.2 | 99.5, 0.5 | 1.7 |
| QHP | 3.4 | 99.6, 0.4 | 1.6 |

[a] Mon = Monomer
[b] Agg = Aggregates
[c] Others = Fragments, low molecular weight proteins The correlation of % IEC pre-peak area, deamidation and Moxetumomab pasudotox biological activity has been previously discussed above. The data in table XIII shows that the IEC pre-peak area of Moxetumomab pasudotox in the hydroxyapatite product pool of Example 3 was over 2-fold higher than in Example 2. Phenyl 650M and Q Sepharose HP chromatography reduced the IEC pre-peak area by approximately 5% to less than 3.5%, providing a biologically active product.

Table XIII demonstrates that Fractogel TMAE (M) chromatography significantly increase in monomer purity and removed most of the low molecular weight proteins and fragments from the process stream as measured by high performance size exclusion chromatography (HPSEC). Phenyl 650 M chromatography provided additional clearance of fragments and aggregates and generated a Moxetumomab pasudotox product pool that had 99.5% monomer purity by HPSEC analysis.

Table XIV shows the clearance of process-related contaminants including host cell proteins, DNA and endotoxins.

TABLE XIV

Clearance of Process-Related Contaminants in Purification Process

| Step | HCP (ng/mg) | Endotoxin (EU/mg) | DNA (ng/mg) |
|---|---|---|---|
| UFDF2 | 1345 | 107965 | 0.72 |
| TMAE | 70.4 | 130.4 | $<0.7.0 \times 10^{-3}$ |
| HA | 37.3 | 11.9 | $<0.8 \times 10^{-3}$ |
| Phenyl | 4.2 | 2.8 | $<1.4 \times 10^{-3}$ |
| QHP | 2.8 | 0.092 | None detected |

The data in Table XIV demonstrates the effectiveness of the Fractogel TMAE (M) capture step and hydroxyapatite chromatography in removing process-related contaminants from the Moxetumomab pasudotox process stream. Fractogel TMAE (M) chromatography reduced host cell protein concentrations approximately 20-fold and endotoxin concentrations over 800-fold. Fractogel TMAE (M) chromatography achieved clearance of host cell DNA to below the limit of quantitation. Hydroxyapatite chromatography further reduced the host cell protein concentration approximately 2-fold and endotoxin concentrations over 10-fold. Phenyl 650 M chromatography achieved a nearly 9-fold reduction in host cell protein concentration whereas Q Sepharose HP chromatography provided an additional 30-fold reduction in endotoxin concentration.

3. Summary

A comparable drug substance yield was achieved for the two purifications described in Examples 2 and 3. The data demonstrates the reproducibility of the renaturation and purification methods described herein and the capability of these methods to generate high quality drug substance suitable for clinical trials.

The methods described herein also contribute to a significant improvement in overall process yields compared to previous Moxetumomab pasudotox renaturation and purification methods. These process improvements will play an important role in making the manufacture of Moxetumomab pasudotox an economically viable process.

Example 4: Fractogel TMAE (M) Cleaning Method

Operation of an economically viable purification process dictates that chromatography resins are used for multiple production cycles. This requires efficient column cleaning methods and the demonstration that product as well as product- and process-related contaminants are removed from the column to below acceptable levels prior to the start of the next purification cycle.

Low refold titers, but high concentrations of product- and process related impurities including aggregates, misfolded proteins, bacterial DNA, host cell proteins and endotoxins pose a significant challenge for post-refold capture columns in E. coli inclusion body-based drug substance manufacturing processes.

For the Moxetumomab pasudotox manufacturing process, most of the impurities were found to bind tightly to the Fractogel TMAE (M) resin and were not efficiently removed from the column with two wash solutions containing either 2 M sodium chloride or unbuffered 8M urea. A buffer containing 8M urea, 0.5M arginine, 50 mM ethanolamine, 2 mM EDTA and 10 mM DTT at pH 9.3 was found to be effective in removing process- and product-related contaminants from Fractogel TMAE (M) resin.

A. Materials and Methods

1. Chromatography Media and Instrumentation

Fractogel TMAE (M) was from EMD. Purifications were performed in a Tricorn 5/200 column. All purifications were performed on an AKTA Explorer chromatography system.

2. Fractogel TMAE (M) Purification and Carry-Over Analysis

Fractogel TMAE (M) purifications were performed as described above. Fractogel TMAE (M) columns were loaded with concentrated and diafiltered refold solution to 20 g protein/L resin. For carry over analysis, Fractogel TMAE columns were run as described above but without protein loading and, where noted, without Triton X-100 wash buffer.

3. Results and Discussion

Figure 11:
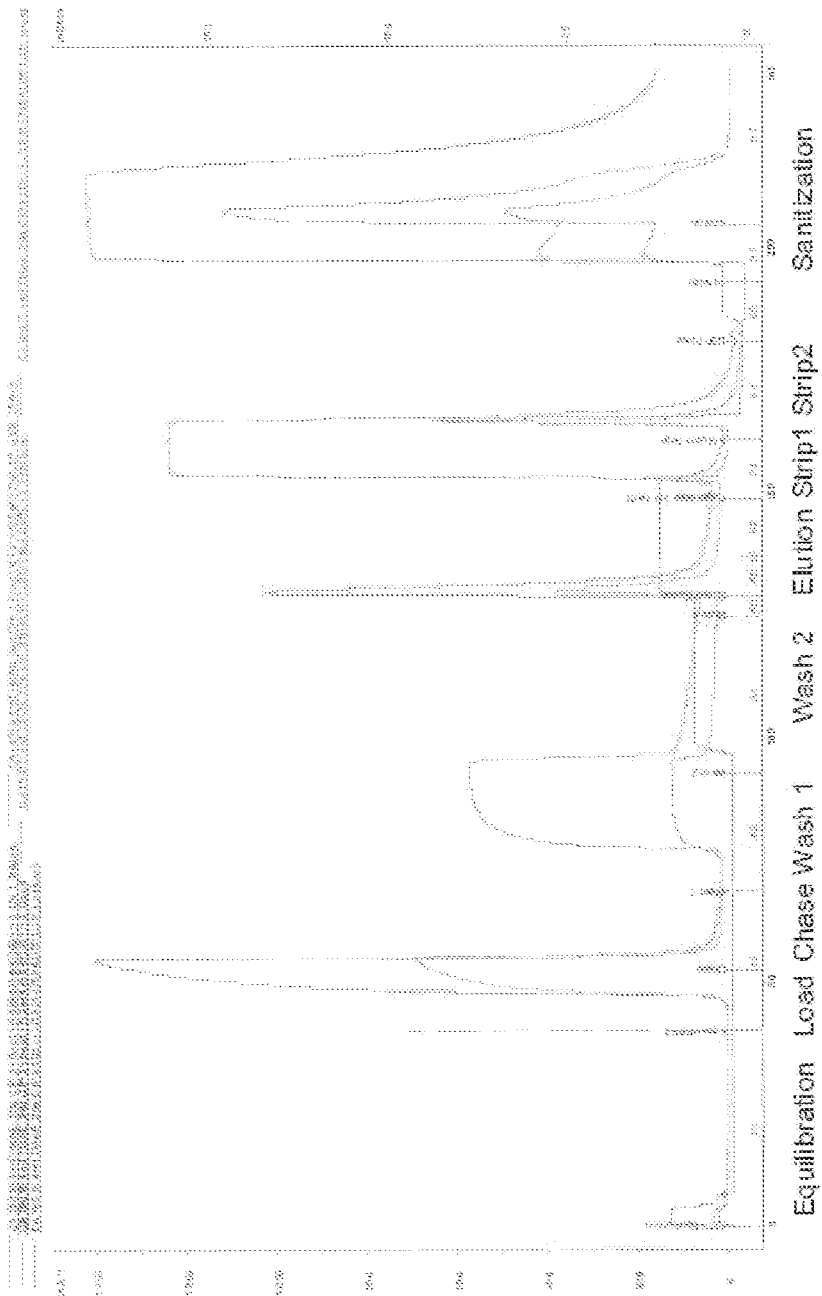
FIG. 11 shows the results of a Fractogel TMAE (M) capture step chromatogram.

FIG. 11 shows a Fractogel TMAE capture step chromatogram using 2M NaCl (Strip 1), 8M urea (Strip 2) and 1N sodium hydroxide as column cleaning and sanitization solutions. The Fractogel TMAE (M) purification sequence is described in Table XV.

TABLE XV

Fractogel TMAE (M) Purification Sequence for FIG. 11

| Step | Buffer | Duration (No. of CVs) |
|---|---|---|
| Equilibration | 20 mM phosphate, pH 7.4 | 10 |
| Load | Not applicable | Not applicable |
| Chase | 20 mM phosphate, pH 7.4 | 3 |
| Wash 1 | 20 mM phosphate, 0.1% Triton X-100, pH 7.4 | 6 |
| Wash 2 | 20 mM phosphate, 100 mM NaCl, pH 7.4 | 8 |
| Elution | 20 mM phosphate, 200 mM NaCl, pH 7.4 | 5 |
| Strip 1 | 2M NaCl | 3 |
| Strip 2 | 8M urea | 5 |
| Water Flush | Water | 3 |
| Sanitization | 1N NaOH | 3 |
| Storage | 0.1N NaOH | 3 |

Several peaks were observed during the column cleaning steps. A blank run without protein load and wash 1 buffer was subsequently performed on the same column Table XVI describes the Fractogel TMAE purification sequence for the blank run.

TABLE XVI

Figure 12:
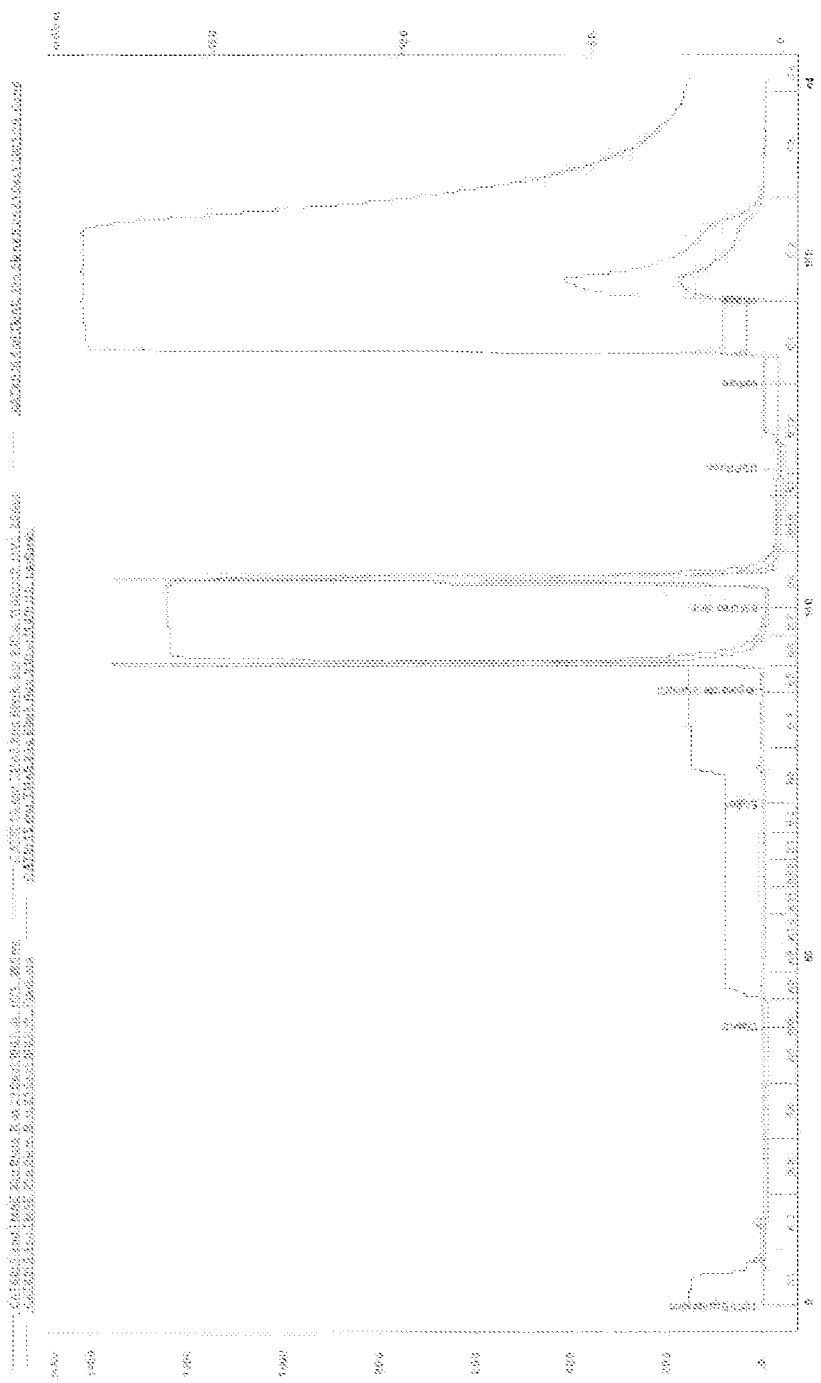
FIG. 12 shows the results of a Fractogel TMAE (M) carryover chromatogram.

Fractogel TMAE (M) Purification Sequence for FIG. 12

| Step | Buffer | Duration (No. of CVs) |
|---|---|---|
| Equilibration | 20 mM phosphate, pH 7.4 | 10 |
| Wash 1 | 20 mM phosphate, 0.1% Triton X-100, pH 7.4 | 6 |
| Wash 2 | 20 mM phosphate, 100 mM NaCl, pH 7.4 | 8 |
| Elution | 20 mM phosphate, 200 mM NaCl, pH 7.4 | 5 |
| Strip 1 | 2M NaCl | 3 |
| Strip 2 | 8M urea | 5 |
| Water Flush | Water | 3 |
| Sanitization | 1N NaOH | 3 |
| Storage | 0.1N NaOH | 3 |

FIG. 12 shows that significant carryover peaks were observed when the previously cleaned column was stripped again with 2M NaCl (Strip 1) and 8 M urea (Strip 2). The same profile was observed for at least two additional runs executed according to table XVI, demonstrating that the above described cleaning and sanitization method did not effectively remove product- and process-related contaminants from the resin.

Based on the observation that a buffer containing 8M urea, 0.5M arginine and 10 mM DTT was able to dissolve *E. coli* inclusion bodies, Moxetumomab pasudotox IB solubilization buffer (50 mM ethanolamine, 8M urea, 0.5M arginine, 2 mM EDTA, 10 mM DTT, pH 9.5) was tested as capture step column cleaning solution. The purification sequence is described in table XVII.

TABLE XVII

Figure 13:
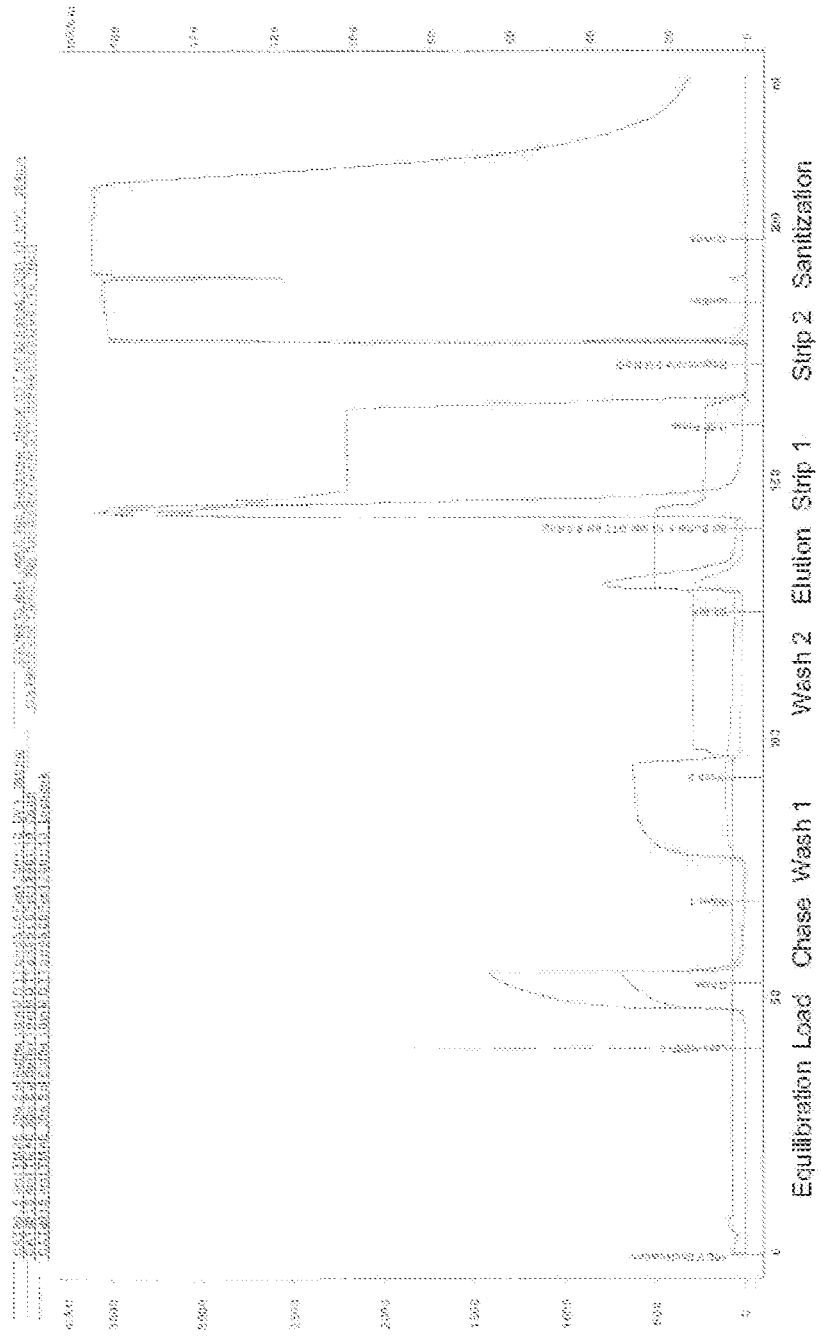
FIG. 13 shows the results of a Fractogel TMAE (M) chromatogram using Moxetumomab pasudotox inclusion body (IB) solubilization buffer for column cleaning.

Fractogel TMAE (M) Purification Sequence for FIG. 13

| Step | Buffer | Duration (No. of CVs) |
|---|---|---|
| Equilibration | 20 mM phosphate, pH 7.4 | 10 |
| Load | Not applicable | Not applicable |
| Chase | 20 mM phosphate, pH 7.4 | 3 |
| Wash 1 | 20 mM phosphate, 0.1% Triton X-100, pH 7.4 | 6 |
| Wash 2 | 20 mM phosphate, 100 mM NaCl, pH 7.4 | 8 |
| Elution | 20 mM phosphate, 200 mM NaCl, pH 7.4 | 5 |
| Strip 1 | 50 mM ethanolamine, 8M urea, 0.5M arginine, 2 mM EDTA, 10 mM DTT, pH 9.5 | 5 |
| Water Flush | Water | 3 |
| Strip 2 | 2M NaCl | 3 |
| Sanitization | 1N NaOH | 3 |
| Storage | 0.1N NaOH | 3 |

FIG. 13 shows a Fractogel TMAE M capture chromatogram with a 5 CV strip using the Moxetumomab pasudotox IB solubilization buffer. A very strong peak was observed when the column was cleaned with IB solubilization buffer (Strip 1); with little or no additional proteins eluting from the column in the subsequent high salt wash (Strip 2) or sanitization step.

Figure 14:
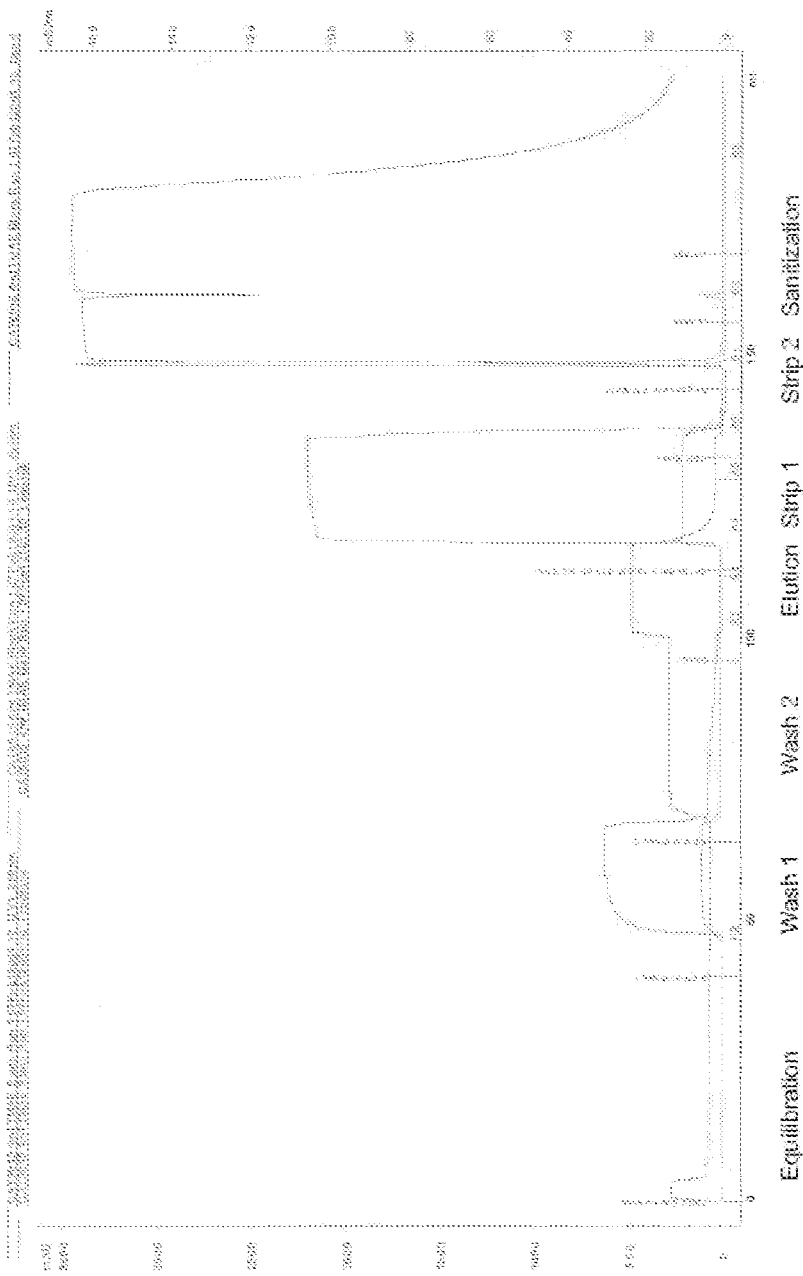
FIG. 14 shows the results of a Fractogel TMAE (M) carry over chromatogram with IB solubilization buffer.

FIG. 14 shows the subsequent Fractogel TMAE (M) chromatogram without protein load. The purification sequence is described in table XVIII.

TABLE XVIII

Figure 15:
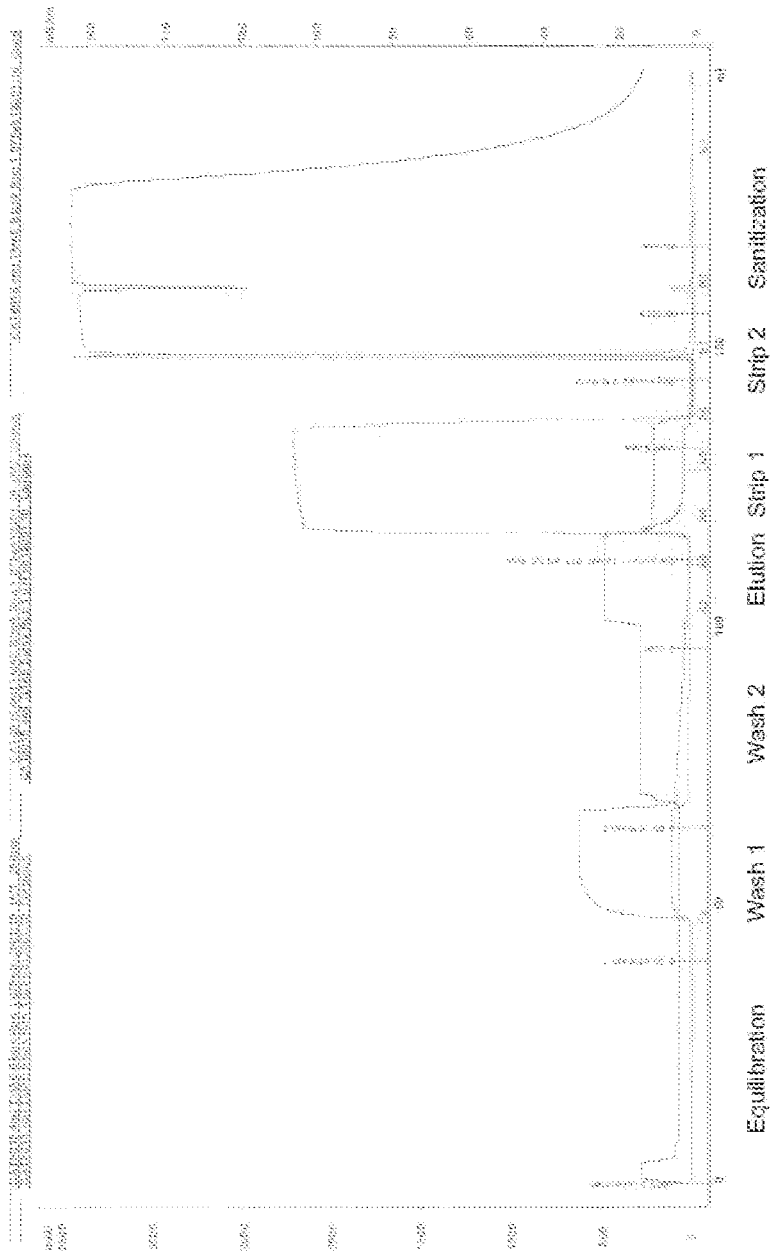
FIG. 15 shows the results of a Fractogel TMAE (M) blank buffer chromatogram with IB solubilization buffer.
Figure 16:
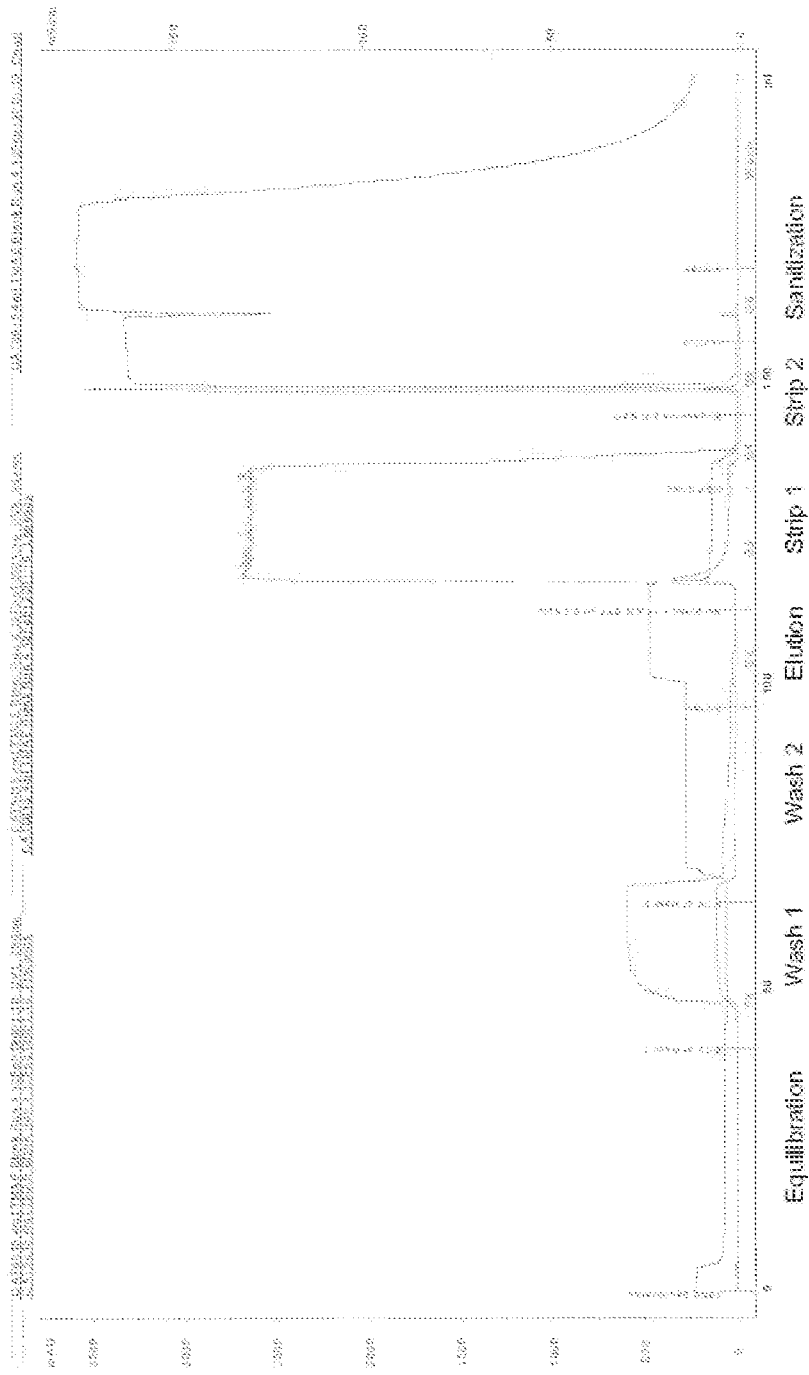
FIG. 16 shows the results of a Fractogel TMAE (M) carry over chromatogram after 9 purification cycles.
Figure 17:
FIG. 17 shows the results of a Representative Capto Blue Sepharose chromatogram.
Figure 18:
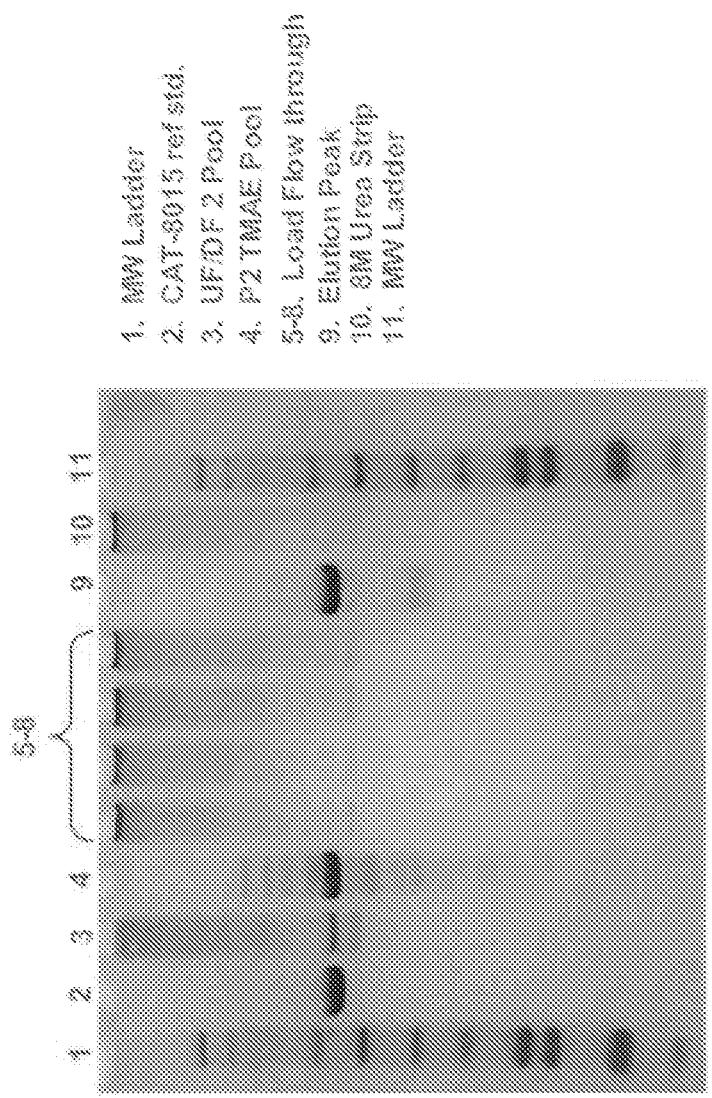
FIG. 18 shows the results of a Non-reduced SDS-PAGE analysis of Capto Blue Sepharose purification fractions shown in FIG. 17.
Figure 19:
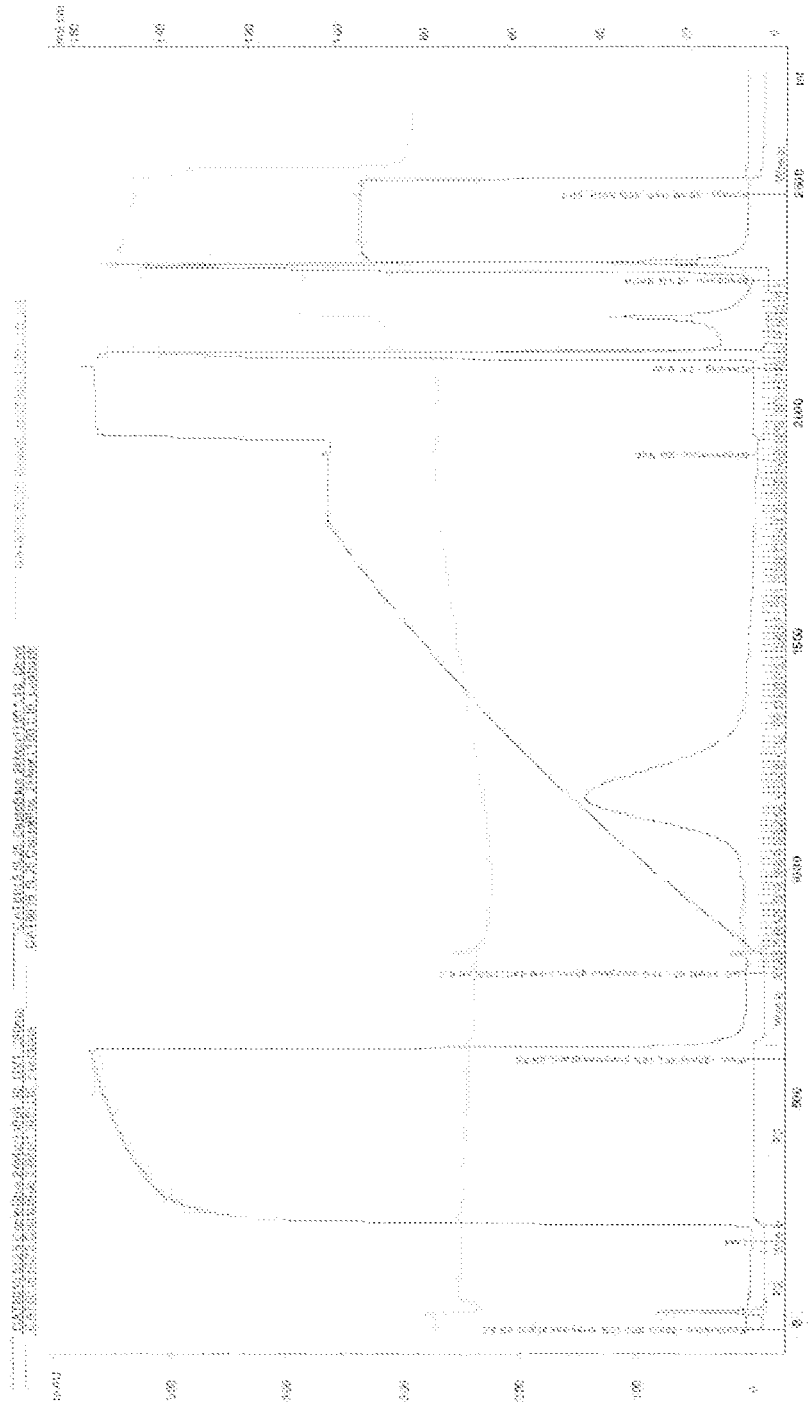
FIG. 19 shows the results of a Representative Capto Blue Sepharose capture step chromatogram.

Fractogel TMAE (M) Purification Sequence for FIGS. 14 to 16

| Step | Buffer | Duration (No. of CVs) |
|---|---|---|
| Equilibration | 20 mM phosphate, pH 7.4 | 10 |
| Wash 1 | 20 mM phosphate, 0.1% Triton X-100, pH 7.4 | 6 |
| Wash 2 | 20 mM phosphate, 100 mM NaCl, pH 7.4 | 8 |
| Elution | 20 mM phosphate, 200 mM NaCl, pH 7.4 | 5 |
| Strip 1 | 50 mM ethanolamine, 8M urea, 0.5M arginine, 2 mM EDTA, 10 mM DTT, pH 9.5 | 5 |
| Water Flush | Water | 3 |
| Strip 2 | 2M NaCl | 3 |
| Sanitization | 1N NaOH | 3 |
| Storage | 0.1N NaOH | 3 |

Carryover of product- and process-related contaminants was not observed. The absorbance peaks observed during the strip and sanitization steps were due to background absorbance of the IB solubilization buffer components (see FIG. 15 for blank buffer chromatogram with new resin). The Fractogel TMAE (M) carry over chromatogram after 9 purification cycles seen in FIG. 16 was identical to the blank buffer chromatogram with new resin seen in FIG. 15, demonstrating that the IB solubilization buffer effectively cleans and regenerates the resin to its original state.

Example 4: Capto Blue Capture

Cibacron Blue Dye chromatography was used to capture Moxetumomab pasudotox from post-refold UF/DF 2 pool under slightly acidic conditions as an alternative to anion exchange capture. The interaction of Moxetumomab pasudotox with the Cibacron Blue dye ligand is multimodal in nature and quite strong. Selective binding of Moxetumomab pasudotox on Cibacron Blue resins can be modulated with ionic components as well as hydrophobic components such as propylene glycol. Capture of Moxetumomab pasudotox by Cibacron Blue Dye as described herein.

A. Materials and Methods

1. Chromatography and Instrumentation

Capto Blue Sepharose was from GE Healthcare. Capto Blue Sepharose purifications were performed in XK16/20 columns (GE Healthcare). All purifications were performed on the AKTA Explorer chromatography system.

2. Purification

Capto Blue Sepharose purifications were performed as described above. Concentrated, diafiltered and adjusted refold solution were loaded onto a Capto Blue column (column volume: 39 mL) up to a load challenge of 10 g Moxetumomab pasudotox/L resin.

3. Results and Discussion

During the loading, a flow-through absorbance signal was seen which can be attributed to non-bound impurities, while nearly all of the Moxetumomab pasudotox product was captured by the Capto Blue Sepharose resin. FIG. 17 shows a representative Capto Blue capture step chromatogram. Selective binding of Moxetumomab pasudotox can be seen in the SDS-PAGE gel in FIG. 18 as very little Moxetumomab pasudotox was detected in the load flow through fractions. Capto Blue Sepharose showed excellent removal of high molecular weight species. As seen in FIG. 18, the UF/DF 2 pool contained high levels of high molecular weight species that were also seen in the flow-through fractions as well as in the 8M urea strip peak but that were not detected in the elution pool. As a result, the elution pool was quite clean when compared to the UF/DF 2 pool.

FIG. 19 shows a second representative Capto Blue Sepharose capture step chromatogram. Table XIX summarizes the performance of the Capto Blue Sepharose purification shown in FIG. 19.

TABLE XIX

Capto Blue Column Performance Summary

| | UF/DF 2 Pool | Capto Blue Pool |
|---|---|---|
| Total Protein (mg; measured by A280) | 583.7 | 54.6 |
| Moxetumomab pasudotox (mg; measured by RP-HPLC) | 58.4 | 53.5 |
| Total Protein Yield (%; measured by A280) | — | 9.4% |
| Moxetumomab pasudotox Yield (%; measured by RP-HPLC) | — | 91.7% |
| HCP (ng/mg; rabbit ELISA) | 74,368 | 16,112 |
| DNA (ng/mg) | $1.66 \times 10^2$ | $2.20 \times 10^1$ |
| SEC - Aggregate (%) | — | 2.4% |
| SEC - Monomer (%) | — | 86.5% |
| SEC - Other (%) | — | 11.1% |

Breakthrough of the non-bound impurities was observed during the load, followed by an elution peak during sodium chloride elution gradient. Table XIX shows that the UF/DF 2 pool contained 583.7 milligram of total protein (measured by absorbance at 280 nm) but only 58.4 milligrams of Moxetumomab pasudotox product (measured by RP-HPLC). The Capto Blue pool contained 58.4 milligrams of total protein, of which 53.5 milligrams were Moxetumomab pasudotox, resulting in a total protein yield of only 9.4%, but a Moxetumomab pasudotox yield of 91.7%. A 4.6-fold reduction in HCP was achieved by the Capto Blue chromatography step. Propylene glycol was also added to the elution buffers in combination with sodium chloride to modulate Moxetumomab pasudotox binding. Elution with sodium chloride alone resulted in a broad elution peak; however, the presence of propylene glycol in the sodium chloride gradient elution sharpened the elution peak and increased product yield.

FIGS. 17-19 demonstrates the reproducibility of the Capto Blue Sepharose purification methods described herein and their capability to selectively capture refolded immunoconjugates, including Moxetumomab pasudotox, from a complex solution consisting of intact product as well as misfolded, aggregated product variants and process-related impurities.

All documents, patents, journal articles and other materials cited in the present application are hereby incorporated by reference.

Although the present invention has been fully described in conjunction with several embodiments thereof with reference to the accompanying drawings, it is to be understood that various changes and modifications can be apparent to those skilled in the art. Such changes and modifications are to be understood as included within the scope of the present invention as defined by the appended claims, unless they depart there from.

What is claimed is:

1. A method of preparing an active immunoconjugate, wherein said immunoconjugate is composed of two polypeptide chains joined by a disulfide bond, the method comprising refolding said immunoconjugate in a fed-batch refolding process in a refold buffer having a pH of 9.5 or less, and purifying the refolded immunoconjugate using a two cycle elution on an ion exchange column, wherein the column is stripped between a first elution and a second elution with a stripping buffer comprising arginine, urea and dithiothreitol (DTT), wherein the stripping buffer comprises 0.25M to about 0.75 M arginine, 7M to about 9 M urea and 9 mM to about 11 mM DTT.

2. The method of claim 1, wherein an amount of the immunoconjugate recovered from the method of preparation is at least three-hundred % (300%) greater than an amount of the immunoconjugate recovered utilizing a method that does not comprise a fed-batch refolding process and/or purification on an ion exchange column that has been stripped using the stripping buffer.

3. The method of claim 2, wherein the polypeptide or immunoconjugate comprises an antibody or antigen binding fragment thereof.

4. The method of claim 3, wherein the antibody or antigen binding fragment comprises a Fab, a Fab', a F(ab')2, a Fd, a single chain Fv or scFv, a disulfide linked Fv, a V-NAR domain, an IgNar, an intrabody, an IgGΔCH2, a minibody, a F(ab')3 a tetrabody, a triabody, a diabody, a single-domain antibody, DVD-Ig, Fcab, mAb², a (scFv)2, or a scFv-Fc.

5. The method of claim 2, wherein the polypeptide or immunoconjugate comprises a toxin.

6. The method of claim 5, wherein the toxin is a *Pseudomonas* exotoxin, or variant thereof.

7. The method of claim 6, wherein said *Pseudomonas* exotoxin, or variant thereof has an amino acid sequence selected from the group consisting of SEQ ID NOs: 16-22.

8. The method of claim 7, wherein said *Pseudomonas* exotoxin, or variant thereof has the amino acid sequence of SEQ ID NO:22.

9. The method of claim 3, wherein said antibody or antigen binding fragment thereof comprises a VH and a VL sequence.

10. The method of claim 9, wherein said VH sequence is selected from the group consisting of SEQ ID NOs: 6-11.

11. The method of claim 9, wherein said VL sequence is selected from the group consisting of SEQ ID NOs: 2, and 12-15.

12. The method of claim 2, wherein the immunoconjugate comprises an anti-CD22 antibody or antigen binding fragment thereof and a PE or variant thereof.

13. The method of claim 12, wherein the immunoconjugate is the Moxetumomab pasudotox immunotoxin comprising the VH-PE38 subunit of SEQ ID NO: 1 and the VL subunit of SEQ ID NO:2.

14. The method of claim 2, wherein the refold buffer has a pH of 9.4.

15. The method of claim 2, wherein the fed batch process uses an addition rate of about 52 mL of solubilized inclusion bodies per L of refold buffer per hour to about 13 mL solubilized inclusion bodies per L refold buffer per hour.

16. The method of claim 15, wherein the fed batch process uses an addition rate of about 35 mL of solubilized inclusion bodies per L of refold buffer per hour to about 17 mL solubilized inclusion bodies per L refold buffer per hour.

17. The method of claim 16, wherein the fed batch process uses an addition rate of about 30 mL of solubilized inclusion bodies per L of refold buffer per hour to about 18 mL solubilized inclusion bodies per L refold buffer per hour.

18. The method of claim 17, wherein the fed batch process uses an addition rate of about 26 mL of solubilized inclusion bodies per L of refold buffer per hour.

19. The method of claim 15, wherein the fed batch process occurs over a period of about 2 to about 8 hours.

* * * * *

SEQUENCE LISTING

```
<160> NUMBER OF SEQ ID NOS: 23

<210> SEQ ID NO 1
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

```
Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Thr Thr Tyr Tyr Pro Asp Thr
50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Leu Val Ser Ala Lys Ala Ser Gly Gly Pro
            115                 120                 125

Glu Gly Gly Ser Leu Ala Ala Leu Thr Ala His Gln Ala Cys His Leu
    130                 135                 140

Pro Leu Glu Thr Phe Thr Arg His Arg Gln Pro Arg Gly Trp Glu Gln
145                 150                 155                 160

Leu Glu Gln Cys Gly Tyr Pro Val Gln Arg Leu Val Ala Leu Tyr Ile
                165                 170                 175

Ala Ala Arg Leu Ser Trp Asn Gln Val Asp Gln Val Ile Arg Ala Leu
            180                 185                 190

Ala Ser Pro Gly Ser Gly Gly Asp Leu Gly Glu Ala Ile Arg Glu Gln
    195                 200                 205

Pro Glu Gln Ala Arg Leu Ala Leu Thr Leu Ala Ala Ala Glu Ser Glu
210                 215                 220

Arg Phe Val Arg Gln Gly Thr Gly Asn Asp Glu Ala Gly Ala Ala Asn
225                 230                 235                 240

Gly Pro Ala Asp Ser Gly Asp Ala Leu Leu Glu Arg Asn Tyr Pro Thr
            245                 250                 255

Gly Ala Glu Phe Leu Gly Asp Gly Gly Asp Val Ser Phe Ser Thr Arg
            260                 265                 270

Gly Thr Gln Asn Trp Thr Val Glu Arg Leu Leu Gln Ala His Arg Gln
            275                 280                 285

Leu Glu Glu Arg Gly Tyr Val Phe Val Gly Tyr His Gly Thr Phe Leu
290                 295                 300

Glu Ala Ala Gln Ser Ile Val Phe Gly Gly Val Arg Ala Arg Ser Gln
305                 310                 315                 320

Asp Leu Asp Ala Ile Trp Arg Gly Phe Tyr Ile Ala Gly Asp Pro Ala
            325                 330                 335

Leu Ala Tyr Gly Tyr Ala Gln Asp Gln Glu Pro Asp Ala Arg Gly Arg
            340                 345                 350

Ile Arg Asn Gly Ala Leu Leu Arg Val Tyr Val Pro Arg Ser Ser Leu
            355                 360                 365

Pro Gly Phe Tyr Arg Thr Ser Leu Thr Leu Ala Ala Pro Glu Ala Ala
    370                 375                 380

Gly Glu Val Glu Arg Leu Ile Gly His Pro Leu Pro Leu Arg Leu Asp
385                 390                 395                 400

Ala Ile Thr Gly Pro Glu Glu Gly Gly Arg Leu Glu Thr Ile Leu
            405                 410                 415

Gly Trp Pro Leu Ala Glu Arg Thr Trp Ile Pro Ser Ala Ile Pro Thr
```

```
                420                 425                 430

Asp Pro Arg Asn Val Gly Gly Asp Leu Asp Pro Ser Ser Ile Pro Asp
        435                 440                 445

Lys Glu Gln Ala Ile Ser Ala Leu Pro Asp Tyr Ala Ser Gln Pro Gly
    450                 455                 460

Lys Pro Pro Arg Glu Asp Leu Lys
465                 470

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Ser Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Ile Leu His Ser Gly Val Pro Ser Arg Phe Ser
50                  55                  60

Gly Ser Gly Ser Gly Thr Asp Tyr Ser Leu Thr Ile Ser Asn Leu Glu
65                  70                  75                  80

Gln Glu Asp Phe Ala Thr Tyr Phe Cys Gln Gln Gly Asn Thr Leu Pro
                85                  90                  95

Trp Thr Phe Gly Cys Gly Thr Lys Leu Glu Ile Lys
            100                 105

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Asp Glu Leu
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Glu Asp Leu
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 5

Arg Glu Asp Leu Lys
1               5

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
                20                  25                  30

Tyr Asp Met Ser Trp Val Arg Gln Thr Pro Glu Lys Cys Leu Glu Trp
            35                  40                  45

Val Ala Tyr Ile Ser Ser Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Leu Val Thr Val Ser Ala
        115                 120

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
                20                  25                  30

Tyr Asp Met Ser Trp Val Arg Gln Thr Pro Glu Lys Cys Leu Glu Trp
            35                  40                  45

Val Ala Tyr Ile Ser Ser Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Tyr Asn Trp Gly Val Leu Phe Ala
            100                 105                 110

Tyr Trp Gly Gln Gly Thr Leu Val Thr Val Ser Ala
        115                 120

<210> SEQ ID NO 8
<211> LENGTH: 124

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr Thr Trp Gly Val Leu Phe Ala
            100                 105                 110

Tyr Trp Gly Gln Gly Thr Leu Val Thr Val Ser Ala
        115                 120

```
<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Ser Thr Tyr Gly Val Leu Phe Ala
            100                 105                 110

Tyr Trp Gly Gln Gly Thr Leu Val Thr Val Ser Ala
        115                 120

```
<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

Met Glu Val Gln Leu Val Glu Ser Gly Gly Gly Leu Val Lys Pro Gly

```
                   1               5                  10                  15
Gly Ser Leu Lys Leu Ser Cys Ala Ala Ser Gly Phe Ala Phe Ser Ile
                20                  25                  30

Tyr Asp Met Ser Trp Val Arg Gln Thr Pro Glu Lys Cys Leu Glu Trp
            35                  40                  45

Val Ala Tyr Ile Ser Ser Gly Gly Thr Thr Tyr Tyr Pro Asp Thr
 50                  55                  60

Val Lys Gly Arg Phe Thr Ile Ser Arg Asp Asn Ala Lys Asn Thr Leu
 65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr His Trp Gly Val Leu Phe Ala
                100                 105                 110

Tyr Trp Gly Gln Gly Thr Leu Val Thr Val Ser Ala
            115                 120
```

<210> SEQ ID NO 11
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Glu Val Gln Leu Val Glu Ser Gly Gly Gly Leu Val Lys Pro Gly
 1               5                  10                  15

Gly Ser Leu Lys Leu Ser Cys Ala Ala Ser Gly Phe Ala Phe Ser Ile
                20                  25                  30

Tyr Asp Met Ser Trp Val Arg Gln Thr Pro Glu Lys Cys Leu Glu Trp
            35                  40                  45

Val Ala Tyr Ile Ser Ser Gly Gly Thr Thr Tyr Tyr Pro Asp Thr
 50                  55                  60

Val Lys Gly Arg Phe Thr Ile Ser Arg Asp Asn Ala Lys Asn Thr Leu
 65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Ser Ser Tyr Gly Val Leu Phe Ala
                100                 105                 110

Tyr Trp Gly Gln Gly Thr Leu Val Thr Val Ser Ala
            115                 120
```

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Asp Ile Gln Met Thr Gln Thr Thr Ser Ser Leu Ser Ala Ser Leu
 1               5                  10                  15

Gly Asp Arg Val Thr Ile Ser Cys Arg Ala Ser Gln Asp Ile Ala Arg
                20                  25                  30

Tyr Leu Asn Trp Tyr Gln Gln Lys Pro Asp Gly Thr Val Lys Leu Leu
            35                  40                  45

Ile Tyr Tyr Thr Ser Ile Leu His Ser Gly Val Pro Ser Arg Phe Ser
```

```
                    50                  55                  60
Gly Ser Gly Ser Gly Thr Asp Tyr Ser Leu Thr Ile Ser Asn Leu Glu
 65                  70                  75                  80

Gln Glu Asp Phe Ala Thr Tyr Phe Cys Gln Gln Gly Asn Thr Leu Pro
                     85                  90                  95

Trp Thr Phe Gly Cys Gly Thr Lys Leu Glu Ile Lys
                100                 105
```

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Asp Ile Gln Met Thr Gln Thr Thr Ser Ser Leu Ser Ala Ser Leu
 1               5                  10                  15

Gly Asp Arg Val Thr Ile Ser Cys Arg Ala Ser Gln Asp Ile His Gly
                20                  25                  30

Tyr Leu Asn Trp Tyr Gln Gln Lys Pro Asp Gly Thr Val Lys Leu Leu
             35                  40                  45

Ile Tyr Tyr Thr Ser Ile Leu His Ser Gly Val Pro Ser Arg Phe Ser
 50                  55                  60

Gly Ser Gly Ser Gly Thr Asp Tyr Ser Leu Thr Ile Ser Asn Leu Glu
 65                  70                  75                  80

Gln Glu Asp Phe Ala Thr Tyr Phe Cys Gln Gln Gly Asn Thr Leu Pro
                     85                  90                  95

Trp Thr Phe Gly Cys Gly Thr Lys Leu Glu Ile Lys
                100                 105
```

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Asp Ile Gln Met Thr Gln Thr Thr Ser Ser Leu Ser Ala Ser Leu
 1               5                  10                  15

Gly Asp Arg Val Thr Ile Ser Cys Arg Ala Ser Gln Asp Ile Gly Arg
                20                  25                  30

Tyr Leu Asn Trp Tyr Gln Gln Lys Pro Asp Gly Thr Val Lys Leu Leu
             35                  40                  45

Ile Tyr Tyr Thr Ser Ile Leu His Ser Gly Val Pro Ser Arg Phe Ser
 50                  55                  60

Gly Ser Gly Ser Gly Thr Asp Tyr Ser Leu Thr Ile Ser Asn Leu Glu
 65                  70                  75                  80

Gln Glu Asp Phe Ala Thr Tyr Phe Cys Gln Gln Gly Asn Thr Leu Pro
                     85                  90                  95

Trp Thr Phe Gly Cys Gly Thr Lys Leu Glu Ile Lys
                100                 105
```

<210> SEQ ID NO 15
<211> LENGTH: 108
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 15

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Gly
            20                  25                  30

Tyr Leu Asn Trp Tyr Gln Gln Lys Pro Asp Gly Thr Val Lys Leu Leu
        35                  40                  45

Ile Tyr Tyr Thr Ser Ile Leu His Ser Gly Val Pro Ser Arg Phe Ser
50                  55                  60

Gly Ser Gly Ser Gly Thr Asp Tyr Ser Leu Thr Ile Ser Asn Leu Glu
65                  70                  75                  80

Gln Glu Asp Phe Ala Thr Tyr Phe Cys Gln Gln Gly Asn Thr Leu Pro
                85                  90                  95

Trp Thr Phe Gly Cys Gly Thr Lys Leu Glu Ile Lys
            100                 105

<210> SEQ ID NO 16
<211> LENGTH: 595
<212> TYPE: PRT
<213> ORGANISM: Pseudomonas exotoxin

<400> SEQUENCE: 16

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Trp Met Ala
                165                 170                 175

Gln Thr Gln Pro Arg Arg Glu Lys Arg Trp Ser Glu Trp Ala Ser Gly
            180                 185                 190

Lys Val Leu Cys Leu Leu Asp Pro Leu Asp Gly Val Tyr Asn Tyr Leu
        195                 200                 205

Ala Gln Gln Arg Cys Asn Leu Asp Asp Thr Trp Glu Gly Lys Ile Tyr
    210                 215                 220

Arg Val Leu Ala Gly Asn Pro Ala Lys His Asp Leu Asp Ile Lys Pro
```

Thr Val Ile Ser His Arg Leu His Phe Pro Glu Gly Gly Ser Leu Ala
225                 230                 235                 240

Ala Leu Thr Ala His Gln Ala Cys His Leu Pro Leu Glu Thr Phe Thr
            245                 250                 255

Arg His Arg Gln Pro Arg Gly Trp Glu Gln Leu Glu Gln Cys Gly Tyr
        260                 265                 270

Pro Val Gln Arg Leu Val Ala Leu Tyr Leu Ala Ala Arg Leu Ser Trp
    275                 280                 285

Asn Gln Val Asp Gln Val Ile Arg Asn Ala Leu Ala Ser Pro Gly Ser
290                 295                 300

Gly Gly Asp Leu Gly Glu Ala Ile Arg Glu Gln Pro Glu Gln Ala Arg
305                 310                 315                 320

Leu Ala Leu Thr Leu Ala Ala Ala Glu Ser Glu Arg Phe Val Arg Gln
            325                 330                 335

Gly Thr Gly Asn Asp Glu Ala Gly Ala Ala Asn Gly Pro Ala Asp Ser
        340                 345                 350

Gly Asp Ala Leu Leu Glu Arg Asn Tyr Pro Thr Gly Ala Glu Phe Leu
    355                 360                 365

Gly Asp Gly Gly Asp Val Ser Phe Ser Thr Arg Gly Thr Gln Asn Trp
370                 375                 380

Thr Val Glu Arg Leu Leu Gln Ala His Arg Gln Leu Glu Glu Arg Gly
385                 390                 395                 400

Tyr Val Phe Val Gly Tyr His Gly Thr Phe Leu Glu Ala Ala Gln Ser
            405                 410                 415

Ile Val Phe Gly Gly Val Arg Ala Arg Ser Gln Asp Leu Asp Ala Ile
        420                 425                 430

Trp Arg Gly Phe Tyr Ile Ala Gly Asp Pro Ala Leu Ala Tyr Gly Tyr
    435                 440                 445

Ala Gln Asp Gln Glu Pro Asp Ala Arg Gly Arg Ile Arg Asn Gly Ala
450                 455                 460

Leu Leu Arg Val Tyr Val Pro Arg Ser Ser Leu Pro Gly Phe Tyr Arg
465                 470                 475                 480

Thr Ser Leu Thr Leu Ala Ala Pro Glu Ala Ala Gly Glu Val Glu Arg
            485                 490                 495

Leu Ile Gly His Pro Leu Pro Leu Arg Leu Asp Ala Ile Thr Gly Pro
        500                 505                 510

Glu Glu Glu Gly Gly Arg Leu Glu Thr Ile Leu Gly Trp Pro Leu Ala
    515                 520                 525

Glu Arg Thr Trp Ile Pro Ser Ala Ile Pro Thr Asp Pro Arg Asn Val
530                 535                 540

Gly Gly Asp Leu Asp Pro Ser Ser Ile Pro Asp Lys Glu Gln Ala Ile
545                 550                 555                 560

Ser Ala Leu Pro Asp Tyr Ala Ser Gln Pro Gly Lys Pro Pro Arg Glu
            565                 570                 575

Asp Leu Lys
        580                 585                 590

Asp Leu Lys
595

<210> SEQ ID NO 17
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Asn
            100                 105                 110

Ala Asp Val Val Ser Leu Thr Cys Pro Val Ala Ala Gly Glu Cys Ala
        115                 120                 125

Gly Pro Ala Asp Ser Gly Asp Ala Leu Leu Glu Arg Asn Tyr Pro Thr
130                 135                 140

Gly Ala Glu Phe Leu Gly Asp Gly Asp Val Ser Phe Ser Thr Arg
145                 150                 155                 160

Gly Thr Gln Asn Trp Thr Val Glu Arg Leu Leu Gln Ala His Arg Gln
                165                 170                 175

Leu Glu Glu Arg Gly Tyr Val Phe Val Gly Tyr His Gly Thr Phe Leu
            180                 185                 190

Glu Ala Ala Gln Ser Ile Val Phe Gly Gly Val Arg Ala Arg Ser Gln
        195                 200                 205

Asp Leu Asp Ala Ile Trp Arg Gly Phe Tyr Ile Ala Gly Asp Pro Ala
    210                 215                 220

Leu Ala Tyr Gly Tyr Ala Gln Asp Gln Glu Pro Asp Ala Arg Gly Arg
225                 230                 235                 240

Ile Arg Asn Gly Ala Leu Leu Arg Val Tyr Val Pro Arg Ser Ser Leu
                245                 250                 255

Pro Gly Phe Tyr Arg Thr Ser Leu Thr Leu Ala Ala Pro Glu Ala Ala
            260                 265                 270

Gly Glu Val Glu Arg Leu Ile Gly His Pro Leu Pro Leu Arg Leu Asp
        275                 280                 285

Ala Ile Thr Gly Pro Glu Glu Glu Gly Gly Arg Leu Glu Thr Ile Leu
    290                 295                 300

Gly Trp Pro Leu Ala Glu Arg Thr Val Val Ile Pro Ser Ala Ile Pro
305                 310                 315                 320

Thr Asp Pro Arg Asn Val Gly Gly Asp Leu Asp Pro Ser Ser Ile Pro
                325                 330                 335

Asp Lys Glu Gln Ala Ile Ser Ala Leu Pro Asp Tyr Ala Ser Gln Pro
            340                 345                 350

Gly Lys Pro Pro Arg Glu Asp Leu Lys
        355                 360
```

<210> SEQ ID NO 18
<211> LENGTH: 344
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Gly Asp Val Ser Phe Ser Thr Arg
    130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Gly Arg Leu Glu Thr Ile Leu
        275                 280                 285

Gly Trp Pro Leu Ala Glu Arg Thr Trp Ile Pro Ser Ala Ile Pro Thr
    290                 295                 300

Asp Pro Arg Asn Val Gly Gly Asp Leu Asp Pro Ser Ser Ile Pro Asp
305                 310                 315                 320

Lys Glu Gln Ala Ile Ser Ala Leu Pro Asp Tyr Ala Ser Gln Pro Gly
                325                 330                 335

Lys Pro Pro Arg Glu Asp Leu Lys
            340
```

<210> SEQ ID NO 19
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 19

Met Trp Glu Gln Leu Glu Gln Cys Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg Asn Ala Leu Ala Ser Pro Gly Ser Gly Gly Asp Leu Gly Glu
        35                  40                  45

Ala Ile Arg Glu Gln Pro Glu Gln Ala Arg Leu Ala Leu Thr Leu Ala
50                  55                  60

Ala Ala Glu Ser Glu Arg Phe Val Arg Gln Gly Thr Gly Asn Asp Glu
65                  70                  75                  80

Ala Gly Ala Ala Asn Gly Pro Ala Asp Ser Gly Asp Ala Leu Leu Glu
                85                  90                  95

Arg Asn Tyr Pro Thr Gly Ala Glu Phe Leu Gly Asp Gly Asp Val
                    100                 105                 110

Ser Phe Ser Thr Arg Gly Thr Gln Asn Trp Thr Val Glu Arg Leu Leu
            115                 120                 125

Gln Ala His Arg Gln Leu Glu Glu Arg Gly Tyr Val Phe Val Gly Tyr
        130                 135                 140

His Gly Thr Phe Leu Glu Ala Ala Gln Ser Ile Val Phe Gly Gly Val
145                 150                 155                 160

Arg Ala Arg Ser Gln Asp Leu Asp Ala Ile Trp Arg Gly Phe Tyr Ile
                165                 170                 175

Ala Gly Asp Pro Ala Leu Ala Tyr Gly Tyr Ala Gln Asp Gln Glu Pro
                    180                 185                 190

Asp Ala Arg Gly Arg Ile Arg Asn Gly Ala Leu Leu Arg Val Tyr Val
            195                 200                 205

Pro Arg Ser Ser Leu Pro Gly Phe Tyr Arg Thr Ser Leu Thr Leu Ala
        210                 215                 220

Ala Pro Glu Ala Ala Gly Glu Val Glu Arg Leu Ile Gly His Pro Leu
225                 230                 235                 240

Pro Leu Arg Leu Asp Ala Ile Thr Gly Pro Glu Glu Glu Gly Gly Arg
                245                 250                 255

Leu Glu Thr Ile Leu Gly Trp Pro Leu Ala Glu Arg Thr Val Val Ile
                    260                 265                 270

Pro Ser Ala Ile Pro Thr Asp Pro Arg Asn Val Gly Gly Asp Leu Asp
            275                 280                 285

Pro Ser Ser Ile Pro Asp Lys Glu Gln Ala Ile Ser Ala Leu Pro Asp
        290                 295                 300

Tyr Ala Ser Gln Pro Gly Lys Pro Pro Arg Glu Asp Leu Lys
305                 310                 315

<210> SEQ ID NO 20
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
            20                  25                  30
```

Asn Trp Thr Val Glu Arg Leu Leu Gln Ala His Arg Gln Leu Glu Glu
         35                  40                  45

Arg Gly Tyr Val Phe Val Gly Tyr His Gly Thr Phe Leu Glu Ala Ala
 50                  55                  60

Gln Ser Ile Val Phe Gly Val Arg Ala Arg Ser Gln Asp Leu Asp
 65                  70                  75                  80

Ala Ile Trp Arg Gly Phe Tyr Ile Ala Gly Asp Pro Ala Leu Ala Tyr
             85                  90                  95

Gly Tyr Ala Gln Asp Gln Glu Pro Asp Ala Arg Gly Arg Ile Arg Asn
            100                 105                 110

Gly Ala Leu Leu Arg Val Tyr Val Pro Arg Ser Ser Leu Pro Gly Phe
            115                 120                 125

Tyr Arg Thr Ser Leu Thr Leu Ala Ala Pro Glu Ala Ala Gly Glu Val
130                 135                 140

Glu Arg Leu Ile Gly His Pro Leu Pro Leu Arg Leu Asp Ala Ile Thr
145                 150                 155                 160

Gly Pro Glu Glu Glu Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Lys Glu
        195                 200                 205

Gln Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 21
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Arg His Arg Gln Pro Arg Gly Trp Glu Gln Leu Pro Thr Gly Ala Glu
 1               5                  10                  15

Phe Leu Gly Asp Gly Gly Asp Val Ser Phe Ser Thr Arg Gly Thr Gln
                20                  25                  30

Asn Trp Thr Val Glu Arg Leu Leu Gln Ala His Arg Gln Leu Glu Glu
            35                  40                  45

Gly Gly Tyr Val Phe Val Gly Tyr His Gly Thr Phe Leu Glu Ala Ala
 50                  55                  60

Gln Ser Ile Val Phe Gly Val Arg Ala Arg Ser Gln Asp Leu Asp
 65                  70                  75                  80

Ala Ile Trp Ala Gly Phe Tyr Ile Ala Gly Asp Pro Ala Leu Ala Tyr
             85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
            115                 120                 125

Tyr Ala Thr Ser Leu Thr Leu Ala Ala Pro Glu Ala Ala Gly Glu Val
130                 135                 140

Glu Arg Leu Ile Gly His Pro Leu Pro Leu Arg Leu Asp Ala Ile Thr
145                 150                 155                 160

```
Gly Pro Glu Glu Ala Gly Gly Arg Leu Glu Thr Ile Leu Trp Pro
            165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Ser Glu
        195                 200                 205

Gln Ala Ile Ser Ala Leu Pro Asp Tyr Ala Ser Gln Pro Gly Lys Pro
    210                 215                 220

Pro Arg Glu Asp Leu Lys
225             230

<210> SEQ ID NO 22
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Val Ser Phe Ser
    130                 135                 140

Thr Arg Gly Thr Gln Asn Trp Thr Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Arg
            180                 185                 190

Ser Gln Asp Leu Asp Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Ser Leu Pro Gly Phe Tyr Arg Thr Ser Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Glu Gly Gly Arg Leu Glu Thr
```

-continued

```
                275                 280                 285
Ile Leu Gly Trp Pro Leu Ala Glu Arg Thr Val Val Ile Pro Ser Ala
    290                 295                 300

Ile Pro Thr Asp Pro Arg Asn Val Gly Gly Asp Leu Asp Pro Ser Ser
305                 310                 315                 320

Ile Pro Asp Lys Glu Gln Ala Ile Ser Ala Leu Pro Asp Tyr Ala Ser
                325                 330                 335

Gln Pro Gly Lys Pro Pro Arg Glu Asp Leu Lys
                340                 345

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Ala Ser Gly Gly
1               5
```